United States Patent
Mutharasan et al.

(10) Patent No.: US 10,078,092 B2
(45) Date of Patent: Sep. 18, 2018

(54) ASSAYS FOR MEASURING BINDING KINETICS AND BINDING CAPACITY OF ACCEPTORS FOR LIPOPHILIC OR AMPHIPHILIC MOLECULES

(71) Applicant: Northwestern University, Evanston, IL (US)

(72) Inventors: Raja Kannan Mutharasan, Chicago, IL (US); C. Shad Thaxton, Chicago, IL (US)

(73) Assignee: Northwestern University, Evanston, IL (US)

( * ) Notice: Subject to any disclaimer, the term of this patent is extended or adjusted under 35 U.S.C. 154(b) by 60 days.

(21) Appl. No.: 15/073,941

(22) Filed: Mar. 18, 2016

(65) Prior Publication Data
US 2016/0274134 A1    Sep. 22, 2016

Related U.S. Application Data

(60) Provisional application No. 62/134,788, filed on Mar. 18, 2015.

(51) Int. Cl.
| | | |
|---|---|---|
| *G01N 33/92* | (2006.01) | |
| *G01N 33/543* | (2006.01) | |
| *G01N 33/553* | (2006.01) | |
| *G01N 33/74* | (2006.01) | |
| *G01N 33/542* | (2006.01) | |

(52) U.S. Cl.
CPC .......... *G01N 33/92* (2013.01); *G01N 33/542* (2013.01); *G01N 33/54346* (2013.01); *G01N 33/553* (2013.01); *G01N 33/743* (2013.01); *G01N 2333/775* (2013.01); *G01N 2800/324* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 5,472,881 A | 12/1995 | Beebe et al. | |
| 6,361,944 B1 | 3/2002 | Mirkin et al. | |
| 6,506,564 B1 | 1/2003 | Mirkin et al. | |
| 7,833,992 B2 | 11/2010 | Vargeese et al. | |
| 8,323,686 B2 | 12/2012 | Mirkin et al. | |
| 9,216,155 B2 | 12/2015 | Thaxton et al. | |
| 9,532,948 B2 | 1/2017 | Mirkin et al. | |
| 2003/0147966 A1 | 8/2003 | Franzen et al. | |
| 2003/0170162 A1 | 9/2003 | Nayfeh et al. | |
| 2004/0053384 A1 | 3/2004 | Sligar et al. | |
| 2004/0158051 A1 | 8/2004 | Ozkan et al. | |
| 2004/0170560 A1 | 9/2004 | Fossheim et al. | |
| 2006/0083781 A1 | 4/2006 | Shastri et al. | |
| 2006/0292174 A1 | 12/2006 | De Los Rios et al. | |
| 2007/0218501 A1* | 9/2007 | Fogelman | G01N 33/721 |
| | | | 435/7.1 |
| 2007/0249555 A1* | 10/2007 | Barbaras | A61K 31/663 |
| | | | 514/47 |
| 2007/0298257 A1 | 12/2007 | Ludwig et al. | |
| 2008/0274454 A1 | 11/2008 | Mirkin et al. | |
| 2008/0306016 A1 | 12/2008 | Mirkin et al. | |
| 2008/0311182 A1 | 12/2008 | Ferrari et al. | |
| 2009/0209629 A1 | 8/2009 | Mirkin et al. | |
| 2009/0324706 A1 | 12/2009 | Mirkin et al. | |
| 2010/0136682 A1 | 6/2010 | Mirkin et al. | |
| 2010/0184844 A1 | 7/2010 | Mirkin et al. | |
| 2010/0233141 A1 | 9/2010 | Polach et al. | |
| 2010/0233270 A1 | 9/2010 | Mirkin et al. | |
| 2011/0020242 A1 | 1/2011 | Zheng et al. | |
| 2011/0052680 A1 | 3/2011 | Hendrickson | |
| 2011/0059156 A9 | 3/2011 | Mirkin et al. | |
| 2011/0111974 A1 | 5/2011 | Mirkin et al. | |
| 2012/0149843 A1 | 6/2012 | Chien et al. | |
| 2012/0244230 A1 | 9/2012 | Mirkin et al. | |
| 2013/0034599 A1 | 2/2013 | Thaxton et al. | |
| 2013/0089614 A1 | 4/2013 | Zhang et al. | |
| 2013/0101512 A1 | 4/2013 | Mirkin et al. | |
| 2013/0149374 A1 | 6/2013 | Lee et al. | |
| 2013/0195759 A1 | 8/2013 | Mirkin et al. | |
| 2014/0005258 A1 | 1/2014 | Mirkin et al. | |
| 2014/0134658 A1 | 5/2014 | Ahrens et al. | |
| 2014/0294927 A1 | 10/2014 | Thaxton et al. | |
| 2015/0064255 A1 | 3/2015 | Thaxton et al. | |
| 2015/0086985 A1 | 3/2015 | Giljohann et al. | |
| 2016/0184226 A1 | 6/2016 | Thaxton et al. | |
| 2016/0186178 A1 | 6/2016 | Radovic-Moreno et al. | |
| 2016/0193361 A1 | 7/2016 | Thaxton et al. | |
| 2016/0194642 A1 | 7/2016 | Gryaznov et al. | |
| 2016/0274134 A1 | 9/2016 | Mutharasan et al. | |
| 2017/0157048 A1 | 6/2017 | Radovic-Moreno et al. | |
| 2017/0175121 A1 | 6/2017 | Gryaznov | |
| 2017/0240960 A1 | 8/2017 | Giljohann et al. | |
| 2017/0306331 A1 | 10/2017 | Mader et al. | |
| 2017/0312365 A1 | 11/2017 | Thaxton et al. | |
| 2017/0354711 A1 | 12/2017 | Thaxton et al. | |
| 2018/0042848 A1 | 2/2018 | Gryaznov et al. | |

FOREIGN PATENT DOCUMENTS

| | | |
|---|---|---|
| CN | 1474831 A | 2/2004 |
| CN | 102036652 A | 4/2011 |
| JP | 2011-507807 | 3/2011 |
| JP | 2011-518826 | 6/2011 |
| KR | 2011/0039798 A | 4/2011 |

(Continued)

OTHER PUBLICATIONS

Azzouni et al. Advanced in Urology, total 18 pages (2012).*
Pollard Mol. Biol. of the Cell vol. 21, p. 4061-4067 (2010).*
Luthi et al. ACS Nano vol. 6, p. 276-285 ( 2012).*
Gao et al. (Anal Chem vol. 80, p. 8822-8827 (2008).*

(Continued)

*Primary Examiner* — Changhwa J Cheu
(74) *Attorney, Agent, or Firm* — Wolf, Greenfield & Sacks, P.C.

(57) ABSTRACT

Aspects of the invention relate to methods for measuring the binding constant of a lipophilic or amphiphilic molecule acceptor for a lipophilic or amphiphilic molecule. Methods involve rapid, cell-free competition assays including a labeled lipophilic or amphiphilic molecule and nanoparticle.

27 Claims, 6 Drawing Sheets

(56) References Cited

FOREIGN PATENT DOCUMENTS

| WO | WO 92/21330 | 12/1992 |
|---|---|---|
| WO | WO 93/21528 A1 | 10/1993 |
| WO | WO 2003/008539 A2 | 1/2003 |
| WO | WO 2005/063201 A2 | 7/2005 |
| WO | WO 2005/063288 A1 | 7/2005 |
| WO | WO 2006/110350 A2 | 10/2006 |
| WO | WO 2006/110350 A3 | 10/2006 |
| WO | WO 2006/138145 A1 | 12/2006 |
| WO | WO 2007/089607 A2 | 8/2007 |
| WO | WO 2007/106683 A2 | 9/2007 |
| WO | WO 2008/106660 A2 | 9/2008 |
| WO | WO 2008/127789 A2 | 10/2008 |
| WO | WO 2009/051451 A2 | 4/2009 |
| WO | WO 2009/073984 A1 | 6/2009 |
| WO | WO 2009/131704 | 10/2009 |
| WO | WO 2011/017456 A2 | 2/2011 |
| WO | WO 2011/017690 A2 | 2/2011 |
| WO | WO 2011/044545 A2 | 4/2011 |
| WO | WO 2011/053940 A2 | 5/2011 |
| WO | WO 2011/072133 A1 | 6/2011 |
| WO | WO 2011/079290 A1 | 6/2011 |
| WO | WO 2011/091065 A2 | 7/2011 |

OTHER PUBLICATIONS

International Search Report and Written Opinion for International Application No. PCT/US2009/002540 dated Jul. 22, 2010.
International Preliminary Report on Patentability for International Application No. PCT/US2009/002540 dated Nov. 4, 2010.
International Search Report and Written Opinion for International Application No. PCT/US2011/021753 dated Oct. 7, 2011.
International Preliminary Report on Patentability for International Application No. PCT/US2011/021753 dated Aug. 2, 2012.
International Search Report and Written Opinion for International Application No. PCT/US2013/027431 dated Jun. 13, 2013.
International Preliminary Report on Patentability for International Application No. PCT/US2013/027431 dated Sep. 4, 2014.
International Search Report and Written Opinion for International Application No. PCT/US2014/050963 dated Dec. 3, 2014.
International Preliminary Report on Patentability for International Application No. PCT/US2014/050963 dated Feb. 25, 2016.
International Search Report and Written Opinion for International Application No. PCT/US2015/062431 dated Feb. 25, 2016.
International Preliminary Report on Patentability for International Application No. PCT/US2015/062431 dated Jun. 8, 2017.
International Search Report and Written Opinion for International Application No. PCT/US2016/067243 dated Apr. 11, 2017.
International Search Report and Written Opinion for International Application No. PCT/US2017/021293 dated Jun. 19, 2017.
International Search Report and Written Opinion for International Application No. PCT/US2017/051930 dated Apr. 11, 2017.
International Search Report and Written Opinion for International Application No. PCT/US2014/056697 dated Mar. 18, 2015.
International Preliminary Report on Patentability for International Application No. PCT/US2014/056697 dated Mar. 31, 2016.
Acton et al., Identification of scavenger receptor SR-BI as a high density lipoprotein receptor. Science. Jan. 26, 1996;271(5248):518-20.
Akhter et al., Gold nanoparticles in theranostic oncology: current state-of-the-art. Expert Opin Drug Deliv. Oct. 2012;9(10):1225-43. Epub Aug. 16, 2012.
Chen et al., Kinetics and thermodynamics of DNA hybridization on gold nanoparticles. Nucleic Acids Res. Jun. 2009;37(11):3756-65. doi: 10.1093/nar/gkp230. Epub Apr. 20, 2009.
Cheng et al., Interdigitated phospholipid/alkanethiol bilayers assembled on APTMS-supported gold colloid electrodes. Electroanalysis. 2004;16(1-2):127-31. doi:10.1002/elan.200302929.
Chromy, B. et al., "Different Apolipoproteins Impact Nanolipoprotein Particle Formation," J. Am. Chem. Soc., 2007, 129 (46), 14348-14354.

Cormode, D.P. et al., "Nanocrystal Core High-Density Lipoproteins: A Multimodality Contrast Agent Platform," Nano Lett., 2008, 8 (11), 3715-3723.
Daniel et al., Gold nanoparticles: assembly, supramolecular chemistry, quantum-size-related properties, and applications toward biology, catalysis, and nanotechnology. Chem Rev. Jan. 2004;104(1):293-346.
Dhar et al., Polyvalent oligonucleotide gold nanoparticle conjugates as delivery vehicles for platinum (IV) warheads. J Am Chem Soc. Oct. 21, 2009;131(41):14652-3. doi: 10.1021/ja907182.
Elbakry, A. et al., "Layer-by-Layer Assembled Gold Nanoparticles for siRNA Delivery," Nano Lett., 2009, 9 (5), 2059-2064.
Fan, H. et al., "Self-Assembly of Ordered, Robust, Three-Dimensional Gold Nanocrystal/Silica Arrays," Science, 2004, 403, 567-571.
Frias, J. C. et al., "Recombinant HDL-Like Nanoparticles: A Specific Contrast Agent for MRI of Atherosclerotic Plaques," J. Am. Chem. Soc., 2004, 126 (50), 16316-16317.
Frias, J. C. et al., "Properties of a Versatile Nanoparticle Platform Contrast Agent to Image and Characterize Atherosclerotic Plaques by Magnetic Resonance Imaging," Nano Lett., 2006, 6 (10), 2220-2224.
Giljohann et al., Gold nanoparticles for biology and medicine. Angew Chem Int Ed Engl. Apr. 26, 2010;49(19):3280-94. doi: 10.1002/anie.200904359.
Giljohann et al., Oligonucleotide loading determines cellular uptake of DNA-modified gold nanoparticles. Nano Lett. Dec. 2007;7(12):3818-21. Epub Nov. 13, 2007.
Godard, G. et al., "Antisense Effects of Cholesterol-Oligodeoxynucleotide Conjugates Associated with Poly(alkylcyanoacrylate) Nanoparticles," Eur. J. Biochem., 1995, 232 (2), 404-410.
Goncalves et al., Uptake of high density lipoprotein (HDL) cholesteryl esters by human acute leukemia cells. Leuk Res. Aug. 2005;29(8):955-9. Epub Feb. 24, 2005.
Graziani et al., Uptake of a cholesterol-rich emulsion by breast cancer. Gynecol Oncol. Jun. 2002;85(3):493-7.
Grijalvo et al., Oligonucleotide delivery: a patent review (2010-2013). Expert Opin Ther Pat. Jul. 2014;24(7):801-19. doi:10.1517/13543776.2014.915944. Epub May 5, 2014.
Han et al., Drug and gene delivery using gold nanoparticles. NanoBiotechnology. Mar. 2007;3(1):40-5.
Hashmi et al., Gold catalysis. Angew Chem Int Ed Engl. Dec. 4, 2006;45(47):7896-936.
Hashmi, Gold-catalyzed organic reactions. Chem Rev. Jul. 2007;107(7):3180-211. Epub Jun. 20, 2007.
He et al., Phospholipid-stabilized Au-nanoparticles. Biomacromolecules. May-Jun. 2005;6(3):1224-5.
Hurst, S. et al., "Maximizing DNA Loading on a Range of Gold Nanoparticle Sizes," Anal. Chem., 2006, 78 (24), 8313-8318.
Jones, Simultaneous labeling of lipoprotein intracellular trafficking in pigeon monocyte-derived macrophages. Am J Pathol. Mar. 1997;150(3):1113-24.
Khmelinskaia et al., Effect of anchor positioning on binding and diffusion of elongated 3D DNA nanostructures on lipid membranes. J. Phys. D: Appl. Phys. Apr. 13, 2016;49(19):194001.
Kim, S. et al., "Systemic and Specific Delivery of Small Interfering RNAs to the Liver Mediated by Apolipoprotein A-I," Mol. Ther., 2007, 15 (6), 1145-1152.
Kong et al., Cationic lipid-coated gold nanoparticles as efficient and non-cytotoxic intracellular siRNA delivery vehicles. Pharm Res. Feb. 2012;29(2):362-74. doi: 10.1007/s11095-011-0554-y. Epub Aug. 13, 2011.
Leander, D., "Mixed-Monolayer Gold Nanoparticles for Cancer Therapeutics," Nanoscape, 2010, 7 (1), 11-14.
Lin et al., Gold nanoparticle delivery of modified CpG stimulates macrophages and inhibits tumor growth for enhanced immunotherapy. PLoS One. May 15, 2013;8(5):e63550. doi: 10.1371/journal.pone. 0063550. Print 2013.
Luthi et al., Nanotechnology for synthetic high-density lipoproteins. Trens Mol Med. Dec. 2010;16(12):553-60. doi: 10.1016/j.molmed. 2010.10.006. Epub Nov. 17, 2010.

(56) References Cited

OTHER PUBLICATIONS

Luthi et al., Tailoring of biomimetic high-density lipoprotein nanostructures changes cholesterol binding and efflux. ACS Nano. Jan. 24, 2012;6(1):276-85. doi: 10.1021/nn2035457. Epub Dec. 1, 2011.

Lytton-Jean et al., A thermodynamic investigation into the binding properties of DNA functionalized gold nanoparticle probes and molecular fluorophore probes. J Am Chem Soc. Sep. 21, 2005;127(37):12754-5.

Matsunaga, T. et al., "Biomagnetic Nanoparticle Formation and Application," Supramolecular Science, 1998, 5 (3-4), 391-394.

McMahon et al., Biomimetic high density lipoprotein nanoparticles for nucleic acid delivery. Nano Lett. Mar. 9, 2011;11(3):1208-14. doi: 10.1021/nl1041947. Epub Feb. 14, 2011.

Mirza et al., Preparation and characterization of doxorubicin functionalized gold nanoparticles. Eur J Med Chem. May 2011;46(5):1857-60. doi: 10.1016/j.ejmech.2011.02.048. Epub Feb. 24, 2011.

Niemeyer, C. et al., "Bifunctional DNA-Gold Nanoparticle Conjugates as Building Blocks for the Self-Assembly of Cross-Linked Particle Layers," Biochemical and Biophysical Research Communications, 2003, 311 (4), 995-999.

Patel et al., Peptide antisense nanoparticles. Proc Natl Acad Sci U S A. Nov. 11, 2008;105(45):17222-6. doi:10.1073/pnas. 0801609105.

Paul, New Way to Kill Lymphoma without Chemotherapy uses Golden Nanoparticles. Feinberg School of Medicine: Northwestern University. Jan. 22, 2013. 4 pages. ww.feinberg.northwestern.edu/news/2013/01/lymphoma_nanoparticales.html.

Plant et al., Self-assembled phospholipid/alkanethiol biomimetic bilayers on gold. Langmuir. 1993;9:2764-7.

Rana et al., Monolayer coated gold nanoparticles for delivery applications. Adv Drug Deliv Rev. Feb. 2012;64(2):200-16. doi: 10.1016/j.addr.2011.08.006. Epub Sep. 6, 2011.

Rosi et al., Oligonucleotide-modified gold nanoparticles for intracellular gene regulation. Science. May 19, 2006;312(5776):1027-30.

Rothblat et al., Cell cholesterol efflux: integration of old and new observations provides new insights. J Lipid Res. May 1999;40(5):781-96.

Shahzad et al., Targeted delivery of small interfering RNA using reconstituted high-density lipoprotein nanoparticles. Neoplasia. Apr. 2011;13(4):309-19.

Shin et al., pH-responsive high-density lipoprotein-like nanoparticles to release paclitaxel at acidic pH in cancer chemotherapy. Int J Nanomedicine. 2012;7:2805-16. doi: 10.2147/IJN.S29817. Epub Jun. 6, 2012.

Thaxton, C.S. et al., "Templated Spherical High Density Lipoprotein Nanoparticles," J. Am. Chem. Soc., 2009, 131 (4), 1384-1385.

Tiwari et al., Functionalized gold nanoparticles and their biomedical applications. Nanomaterials. 2011;1:31-63. doi: 10.3390/nano1010031.

Tripathy et al., High Density Lipoprotein Nanoparticles Deliver RNAi to Endothelial Cells to Inhibit Angiogenesis. Part Part Syst Charact. Nov. 1, 2014;31(11):1141-1150.

Wei et al., Polyvalent immunostimulatory nanoagents with self-assembled CpG oligonucleotide-conjugated gold nanoparticles. Angew Chem Int Ed Engl. Jan. 27, 2012;51(5):1202-6. doi:10.1002/anie. 201105187. Epub Dec. 21, 2011.

Yang et al., Biomimetic, synthetic HDL nanostructures for lymphoma. Proc Natl Acad Sci U S A. Feb. 12, 2013;110(7):2511-6. doi: 10.1073/pnas.1213657110. Epub Jan. 23, 2013.

Zhang et al., Self-assembled monolayers of terminal alkynes on gold. J Am Chem Soc. Apr. 25, 2007;129(16):4876-7. Epub Mar. 31, 2007.

\* cited by examiner

ASSAYS FOR MEASURING BINDING KINETICS AND BINDING CAPACITY OF ACCEPTORS FOR LIPOPHILIC OR AMPHIPHILIC MOLECULES

RELATED APPLICATIONS

This Application claims priority under 35 U.S.C. § 119(e) to U.S. Provisional Application Ser. No. 62/134,788, entitled "ASSAYS FOR MEASURING BINDING KINETICS AND BINDING CAPACITY OF ACCEPTORS FOR LIPOPHILIC OR AMPHIPHILIC MOLECULES" filed on Mar. 18, 2015, which is herein incorporated by reference in its entirety.

FIELD OF INVENTION

The present invention relates generally to the use of nanoparticles in assays for monitoring the binding of lipophilic or amphiphilic molecules.

BACKGROUND OF THE INVENTION

Coronary heart disease, which can manifest as heart attacks or sudden death from lethal arrhythmias, is the number one killer in the U.S. and worldwide. Accurate estimation of cardiovascular disease risk is a critical first step in applying life-saving preventative therapies to high risk populations. State-of-the-art methods to ascertain risk, however, remain imperfect. Evidence shows that measuring Cholesterol efflux capacity of a certain human serum fraction significantly enhances prediction accuracy of cardiovascular risk. Measurement of an aspect of Reverse Cholesterol Transport (RCT) with an assay that involves cultured cells and human serum samples improves the accuracy of clinical risk assessment for heart disease (Khera et al. (2011) *N. Engl. J. Med.* 364:127). However, because this assay entails tissue culture techniques, radiolabeled cholesterol, and a 72-hour turnaround time, its clinical utility is limited.

SUMMARY OF THE INVENTION

Quantifying cholesterol transport in complex biological matrices is critically important because of the central role cholesterol balance or overload plays in many human pathologies, such as heart disease (Lusis (2000) *Nature* 407:233). Cholesterol is a hydrophobic molecule minimally soluble in the aqueous milieu of biological systems, yet it is found in millimolar quantities in blood, owing to solubilization in lipid carriers known as lipoproteins which bind and transport cholesterol. Despite the important role cholesterol-lipoprotein interactions have in understanding cholesterol transport, the dissociation constant ($K_D$) of cholesterol from lipoprotein-containing serum fractions remains unknown. Of particular interest is the strength of cholesterol interactions with high density lipoproteins (HDL), as these structures mediate cholesterol clearance from peripheral tissues, a process termed Reverse Cholesterol Transport (RCT) (Rosenson et al. (2012) *Circulation* 125:1905). A simple, automatable assay measuring serum affinity for lipophilic or amphiphilic molecules, such as cholesterol is highly desirable.

Disclosed herein is a nanoparticle-enabled, rapid and cell-free competition assay which directly measures the affinity of lipophilic or amphiphilic molecule acceptors, including human serum. This method was used to discover the dissociation constant ($K_D$) of serum and a serum fraction enriched in HDL for cholesterol.

Aspects of the invention relate to a method for measuring the equilibrium constant of an acceptor for a molecule, comprising: providing a lipophilic or amphiphilic molecule, wherein the molecule can provide a detectable signal; providing a structure, the structure comprising a nanostructure core and a lipid layer surrounding and attached to the nanostructure core, wherein the structure quenches the signal of the molecule when the structure and the molecule are proximate; providing an acceptor; allowing the acceptor to compete with the structure for binding with the molecule; and measuring the signal, wherein the level of the signal correlates with the equilibrium constant of the acceptor for the molecule.

In certain embodiments, the method further comprises increasing the amount of acceptor provided. In certain embodiments, the method further comprises increasing the amount of structure provided.

In certain embodiments, increasing the amount of acceptor provided leads to an increase in signal. In certain embodiments, increasing the amount of structure provided leads to a decrease in signal. In certain embodiments, increasing or decreasing the amount of molecule improves the signal to noise ratio of the system.

In certain embodiments, the method is a component of an assay. In certain embodiments, the method is a component of a diagnostic assay. In certain embodiments, the method is a method for assessing cardiovascular risk in a subject.

Other aspects of the invention relate to a kit for measuring an equilibrium constant of an acceptor for a molecule, comprising: a lipophilic or amphiphilic molecule, wherein the molecule can provide a detectable signal; and a structure, the structure comprising a nanostructure core and a lipid layer surrounding and attached to the nanostructure core, wherein the structure quenches the signal of the molecule when the structure and the molecule are proximate.

In certain embodiments, the kit further comprises instructions for use of the kit for measuring the equilibrium constant of the acceptor for the molecule.

Other aspects of the invention relate to a system for measuring an equilibrium constant of an acceptor for a molecule, comprising: a sample, the sample comprising: a lipophilic or amphiphilic molecule, wherein the molecule can provide a detectable signal; a structure, the structure comprising a nanostructure core and a lipid layer surrounding and attached to the nanostructure core, wherein the structure quenches the signal of the molecule when the structure and the molecule are proximate; an acceptor; and a detector for measuring the signal.

In certain embodiments, the system described further comprises a device configured to calculate the equilibrium constant of the acceptor for the molecule based on the detected signal. In certain embodiments, the system further comprises a radiation source configured to induce the signal.

In certain embodiments of the method, kit, or system herein described, the lipid layer is a bilayer. In certain embodiments of the method, kit or system herein described, the molecule is a steroid or a derivative or analog thereof.

In certain embodiments of the method, kit, or system herein described, the molecule is a lipopolysaccharide or a derivative or analog thereof. In certain embodiments of the method, kit, or system herein described, the molecule is a steroid or a derivative of analog thereof. Several non-limiting classes of steroids include Cholestanes, Cholanes, Pregnanes, Androstanes and Estranes or derivative or analog thereof.

In certain embodiments, of the method, kit, or system herein described, the molecule is BODIPY-cholesterol. In certain embodiments of the method, kit, or system herein described, the signal is fluorescence. In certain embodiments of the method, kit, or system herein described, the signal is fluorescence polarization.

In certain embodiments of the method, kit, or system herein described, the nanostructure core is an inorganic material. In certain embodiments of the method, kit, or system herein described, the nanostructure core is a metal. In certain embodiments of the method, kit, or system herein described, the nanostructure core is gold.

In certain embodiments of the method, kit, or system herein described, the structure further comprises apolipoprotein bound to at least the outer surface of the lipid layer. In certain embodiments of the method, kit, or system herein described, the apolipoprotein is apolipoprotein A-I, apolipoprotein A-II, or apolipoprotein E.

In certain embodiments of the method, kit, or system herein described, the acceptor is a lipoprotein. In certain embodiments of the method, kit, or system herein described, the acceptor is a high-density lipoprotein (HDL). In certain embodiments of the method, kit, or system herein described, the acceptor is a component of serum. In certain embodiments of the method, kit, or system herein described, the serum is human serum. In certain embodiments of the method, kit, or system herein described, the serum is enriched for HDL. In certain embodiments of the method, kit, or system herein described, the serum is depleted for ApoB.

The subject matter of this application involves, in some cases, interrelated products, alternative solutions to a particular problem, and/or a plurality of different uses of structures and compositions.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 1 shows measurement of ApoB-depleted serum at final assay concentrations of 0.00%, 0.16%, 0.32%, 0.49%, and 0.65%, respectively (addition of 0, 5, 10, 15, and 20 ul of ApoB-depleted human serum prepared as described above added to the 200 ul volume containing BODIPY cholesterol and HDL AuNP). The amount of fluorescence recovery rises with the increasing amounts of cholesterol acceptor added. Data points are the mean of wells plated in triplicate.

DETAILED DESCRIPTION

Figure 1:
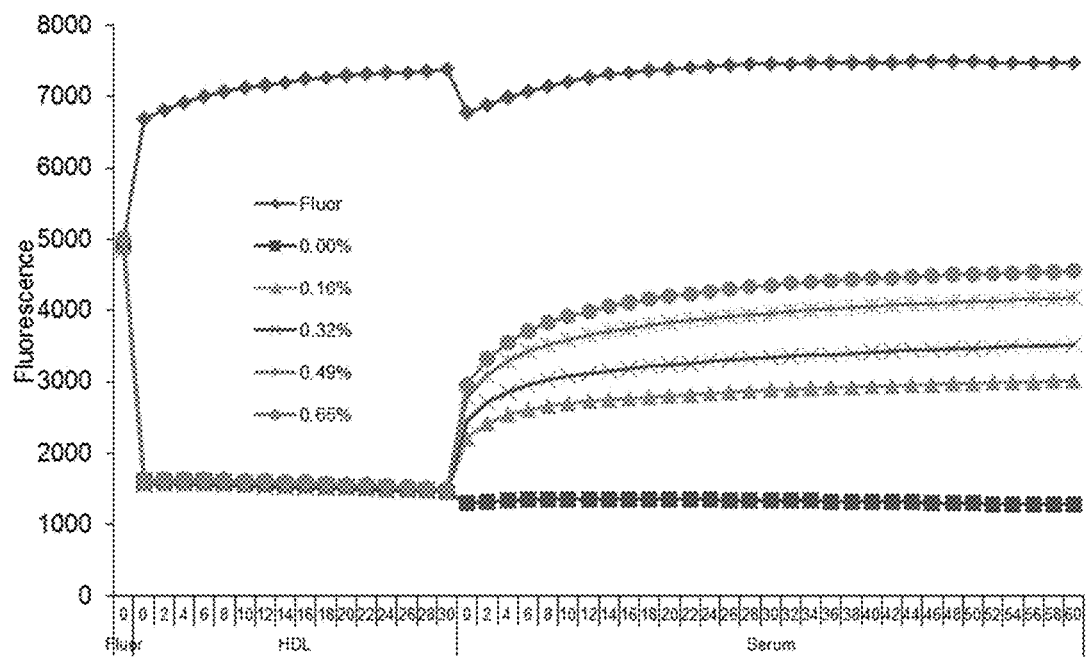
FIG. 1 shows an exemplary binding experiment used to measure binding and kinetics of a cholesterol acceptor, in this case ApoB-depleted human serum. Baseline fluorescence intensity was first recorded in a 6.25 uM solution of BODIPY cholesterol in 100 ul of 20% ethanol in water. Next 100 ul of 500 nM HDL AuNP was added and fluorescence intensity was measured for 30 minutes at 2 minute read intervals. At this point the concentrations of BODIPY cholesterol and HDL AuNP were 312.5 nM and 250 nM, respectively. Finally, cholesterol acceptor was added and fluorescence was measured over 60 minutes.

The invention is based, at least in part, on the development of a rapid, cell-free competition assay for measuring binding between lipophilic or amphiphilic molecules and a lipophilic or amphiphilic molecule acceptor, such as serum or fractions thereof. Methods described herein, using labeled lipophilic or amphiphilic molecules, such as cholesterol analogs, and a lipidated nanoparticle, are rapid and high throughput. These novel assays have widespread applications including: assessing risk of disorders, such as cardiovascular disorders, by measuring lipophilic or amphiphilic molecule binding in patient samples; conducting screens for agents that influence lipophilic or amphiphilic molecule efflux; investigating lipophilic or amphiphilic molecule binding kinetics and binding capacity; and investigating small molecule binding and binding capacity to HDLs (e.g., competition assays).

Aspects of the invention relate to a competition assay that can detect the $K_D$ of lipophilic or amphiphilic molecule acceptors, such as human serum, for lipophilic or amphiphilic molecules, such as cholesterol. When the assay is applied to a sample, such as a human serum sample, it can be used to assess the strength of the interaction between lipophilic or amphiphilic molecules, such as cholesterol, and high density lipoproteins (HDL) within the serum sample. HDL plays a significant role in clearance of cholesterol from peripheral tissues, in a process referred to as Reverse Cholesterol Transport (RCT). Assessing the binding capacity of HDL to cholesterol in a serum sample from a subject provides valuable information on the subject's functional capacity for RCT.

Novel assays described herein have multiple advantages over previous methods for assessing RCT, including: i) Assays described herein are automatable and involve simple and straightforward pipetting steps that can be programmed into laboratory hardware/robotic liquid handling systems. A high-throughput—96- or 384-well format can allow for dozens of samples to be read and processed simultaneously; ii) No radiochemicals need to be used in these assays. Radiolabelled cholesterol, used in previously described assays had to be handled in a specific manner and had to be disposed of carefully. Moreover, most clinical laboratories do not have facilities to carry out radiometric tests; iii) Assays described herein are very rapid—owing to the rapid binding kinetics of both natural lipophilic or amphiphilic molecule acceptors and materials described herein, this test can be performed, including incubation times, within hours with minimal human input. By contrast, previously described Cholesterol efflux assays used in research take 4 days from start to finish; iv) very low serum volumes are required—assays described herein require a serum input on the order of 100 ul from ordinary blood draw tubes. Furthermore, given the stability of lipophilic or amphiphilic molecules, such as cholesterol acceptors in serum, this test has the potential to be done as an "add-on" or "reflex" to routinely collected specimens ordered for other purposes.

Methods described herein involve binding between a lipidated nanoparticle and a labeled lipophilic or amphiphilic molecule, such as a cholesterol analog. As used herein, a "lipidated nanoparticle" refers to a nanoparticle and that is associated with one or more lipids. Lipidated nanoparticles are described further in, and incorporated by reference from PCT/US2009/002540, entitled "Nanostructure Suitable for Sequestering Cholesterol and Other Molecules."

It should be appreciated that any lipophilic or amphiphilic molecules can be compatible with aspect of the invention. As used herein, a lipophilic molecule refers to a molecule that can dissolve in fats, oils, lipids, and non-polar solvents. Examples of lipophilic groups include, but are not limited to, cholesterol, a cholesteryl or modified cholesteryl residue, adamantine, dihydrotesterone, long chain alkyl, long chain alkenyl, long chain alkynyl, olely-lithocholic, cholenic, oleoyl-cholenic, palmityl, heptadecyl, myrisityl, bile acids, cholic acid or taurocholic acid, deoxycholate, oleyl litocholic acid, oleoyl cholenic acid, glycolipids, phospholipids, sphingolipids, isoprenoids, such as steroids, vitamins, such as vitamin E, fatty acids either saturated or unsaturated, fatty acid esters, such as triglycerides, pyrenes, porphyrines, Texaphyrine, adamantane, acridines, biotin, coumarin, fluorescein, rhodamine, Texas-Red, digoxygenin, dimethoxytrityl, t-butyldimethylsilyl, t-butyldiphenylsilyl, cyanine dyes (e.g. Cy3 or Cy5), Hoechst 33258 dye, psoralen, or ibuprofen. The cholesterol moiety may be reduced (e.g. as in cholestan) or may be substituted (e.g. by halogen). A combination of different lipophilic groups in one molecule is also possible. The lipophilic molecule may be a sterol, such as cholesterol.

As used herein, an amphiphilic molecule refers to a molecule that possesses both hydrophilic and lipophilic properties. Several non-limiting examples of amphiphilic compounds include phospholipids, cholesterol, glycolipids, fatty acids, bile acids, saponins and local anaesthetics.

In some embodiments, the molecule is a steroid or a derivative or analog thereof. As used herein, a steroid refers to an organic compound that contains four cycloalkane rings that are joined to each other. Several non-limiting examples of classes of steroids include Cholestane, Cholane, Pregnane, Androstane or Estrane. In some embodiments, the molecule is a lipopolysaccharide or a derivative or analog thereof. As used herein a lipopolysaccharide refers to a molecule consisting of a lipid and a polysaccharide joined by a covalent bond.

The lipophilic or amphiphilic molecules associated with aspects of the invention produce a detectable signal. In some embodiments, the lipophilic or amphiphilic molecule is labeled with a fluorescent label. The terms "fluorescent label", "fluorescent dye", and "fluorophore" are used interchangeably herein to refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 493/503, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxyfluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X, 5(6)-Carboxyfluorescein, 2,7-Dichlorofluorescein, N,N-Bis(2,4,6-trimethylphenyl)-3,4:9,10-perylenebis(dicarboximide, HPTS, Ethyl Eosin, DY-490XL MegaStokes, DY-485XL MegaStokes, Adirondack Green 520, ATTO 465, ATTO 488, ATTO 495, YOYO-1,5-FAM, BCECF, dichlorofluorescein, rhodamine 110, rhodamine 123, YO-PRO-1, SYTOX Green, Sodium Green, SYBR Green I, Alexa Fluor 500, FITC, Fluo-3, Fluo-4, fluoro-emerald, YoYo-1 ssDNA, 2',4',5',7'-Tetra-bromosulfone 1 dsDNA, YoYo-1, SYTO RNASelect, Diversa Green-FP, Dragon Green, EvaGreen, Surf Green EX, Spectrum Green, NeuroTrace 500525, NBD-X, MitoTracker Green FM, LysoTracker Green DND-26, CBQCA, PA-GFP (post-activation), WEGFP (post-activation), F1ASH-CCXXCC, Azami Green monomeric, Azami Green, green fluorescent protein (GFP), EGFP (Campbell Tsien 2003), EGFP (Patterson 2001), Kaede Green, 7-Benzylamino-4-Nitrobenz-2-Oxa-1,3-Diazole, Bexl, Doxorubicin, Lumio Green, and SuperGlo GFP. Those of ordinary skill in the art will know of other suitable fluorescent labels for the assays described herein, or will be able to ascertain such, using routine experimentation.

In some embodiments, the fluorescent label is from the difluoro-boraindacene (4,4-difluoro-4-bora-3a,4a-diaza-s-indacene) family (BODIPY) family. In some embodiments, the labeled lipophilic or amphiphilic molecule is BODIPY-Cholesterol, NBD-Cholesterol or dansyl-Cholesterol or their associated cholesteryl esters. In other embodiments, fluorescent cholesterol analogues that possess intrinsic fluorescence (e.g., dehydroergosterol and cholestatrienol) and those in which a fluorophore or photoreactive group is attached (e.g., NBD-Cholesterol, BODIPY-Cholesterol, and dansyl-cholestanol).

Nanoparticles described herein, such as lipidated gold nanoparticles, have the ability to quench fluorescence emitted by a fluorescently labeled lipophilic or amphiphilic molecules when the fluorescently labeled lipophilic or amphiphilic molecule is in close proximity to the nanoparticle. Accordingly, in assays described herein, binding between the nanoparticle and the fluorescently labeled lipophilic or amphiphilic molecule leads to a reduction in the levels of lipophilic or amphiphilic molecule measured in a sample.

Aspects of the invention involve lipophilic or amphiphilic molecule acceptors. As used herein, a "lipophilic or amphiphilic molecule acceptor" refers to a molecule that can bind to a lipophilic or amphiphilic molecule. A lipophilic or amphiphilic molecule acceptor may be involved in transporting a lipophilic or amphiphilic molecule, such as cholesterol, to the liver from peripheral tissues. A lipophilic or amphiphilic molecule acceptor used in assays described herein can be serum, such as human serum. The serum can be enriched for HDLs. In some embodiments, the serum is depleted for Apolipoprotein B (ApoB). Addition of a lipophilic or amphiphilic molecule acceptor, such as a cholesterol acceptor, to assays described herein causes competition for cholesterol binding with the nanoparticle and causes the fluorescent signal to recover.

As used herein, an acceptor refers to a molecule that binds cholesterol. Examples of an acceptor includes, but it is not limited to, apolipoprotein A1 (ApoA1), high density lipoprotein (HDL), albumin, serum, including human serum, or apolipoprotein B (ApoB)-depleted human serum.

Measurement of fluorescence in assays described herein, following addition of a cholesterol acceptor can be used to assay levels of HDL in a sample and to determine binding and kinetics of a cholesterol acceptor. Since a low HDL level in serum can correlate with an increased risk of disorders associated with cholesterol, such as cardiovascular disorders, assays described herein can contribute to assessing a subject's risk of developing a disorder associated with cholesterol, such as a cardiovascular disorder.

It should be appreciated that in assays described herein a detectable signal, such as fluorescence, can be measured according to any method known in the art. In some aspects, samples are processed in multi-well plates, such as 96-well or 384-well plates and fluorescence is measured using a plate reader. Systems associated with the invention can be configured such that fluorescence is measured and then correlated with outputs such as the binding constant of a lipophilic or amphiphilic molecule acceptor for a lipophilic or amphiphilic molecule.

As used herein, "binding constant" or "association constant" refers to a mathematical constant that describes the binding affinity between two molecules at equilibrium. It should be appreciated that methods described herein can also be used to measure dissociation constants.

Any type of detectable label can be compatible with aspects of the invention. As used herein, a detectable label refers to a moiety, the presence of which can be ascertained directly or indirectly. Generally, detection of a label involves an emission of energy by the label. The label can be detected directly by its ability to emit and/or absorb photons or other atomic particles of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Other detectable labels include radioactive isotopes such as P32 or H3, luminescent markers such as fluorochromes, optical or electron density markers, etc., or epitope tags such as the FLAG epitope or the HA epitope, biotin, avidin, and enzyme tags such as horseradish peroxidase, bb-galactosidase, etc. The label may be bound to a peptide during or following its synthesis.

Non-limiting examples of the types of labels that can be compatible with aspects of the claimed invention include enzymes, radioisotopes, fluorescent compounds, colloidal metals, chemiluminescent compounds, and bioluminescent compounds. Those of ordinary skill in the art will know of other suitable labels for the molecules described herein, or will be able to ascertain such, using routine experimentation. Furthermore, the coupling or conjugation of these labels to the molecules of the invention can be performed using standard techniques common to those of ordinary skill in the art.

Another labeling technique consists of coupling molecules described herein to low molecular weight haptens. These haptens can then be specifically altered by means of a second reaction. For example, haptens such as biotin, can be used, which can react with avidin, or dinitrophenol, pyridoxal, or fluorescein, which can react with specific anti-hapten antibodies. Non-limiting examples of haptens include digoxigenin, Alexa Fluor 488, Biotin-X SE, Biotin-XX SE, Biotin-XX SSE, BODIPY FL-X SE, BODIPY FL STP ester, Cascade Blue acetyl azide, Dansyl-X SE, DSB-X biotin SE, Lucifer yellow iodoacetamide, 5(6)-TAMRA-X SE, Rhodamine Red-X SE, Texas Red-X SE. Examples of corresponding antibodies for hapten conjugation included nut are not limited to Anti-Alexa Fluor 488 dye, Anti-digoxigenin, Anti-biotin, Anti-BODIPY FL dye, Anti-Cascade Blue dye, Anti-DNP, anti-DNP-KLH, anti-biotin, Anti-fluorescein/Oregon Green dye, Anti-lucifer yellow, Anti-fluorescein/Oregon Green dye and Anti-tetramethylrhodamine.

A further category of detectable labels includes diagnostic and imaging labels (generally referred to as in vivo detectable labels) such as for example magnetic resonance imaging (MRI): Gd(DOTA); for nuclear medicine: 201Tl, gamma-emitting radionuclide 99mTc; for positron-emission tomography (PET): positron-emitting isotopes, (18)F-fluorodeoxyglucose ((18)FDG), (18)F-fluoride, copper-64, gadodiamide, and radioisotopes of Pb(II) such as 203Pb; 111In.

The conjugations or modifications described herein employ routine chemistry, which chemistry does not form a part of the invention and which chemistry is well known to those skilled in the art of chemistry. The use of protecting groups and known linkers such as mono- and hetero-bifunctional linkers are well documented in the literature and will not be repeated here. As used herein, "conjugated" means two entities stably bound to one another by any physio-chemical means. In some aspects, it is important that the nature of the attachment is such that it does not impair substantially the effectiveness of either entity. Any covalent or non-covalent linkage known to those of ordinary skill in the art can be employed for conjugation. In some embodiments, covalent linkage is preferred. Noncovalent conjugation includes hydrophobic interactions, ionic interactions, high affinity interactions such as biotin-avidin and biotin-streptavidin complexation and other affinity interactions. Such means and methods of attachment are well known to those of ordinary skill in the art.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The term "mass-tag" as used herein refers to any moiety that is capable of being uniquely detected by virtue of its mass using mass spectrometry (MS) detection techniques. Examples of mass-tags include electrophore release tags such as N-[3-[4'-](p-Methoxytetrafluorobenzy^oxy)phenyl]-S-methylglyceronyllisonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360,8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

Primary labels include but are not limited to radioisotopes (e.g. tritium, 32P, 33P, 35S, 14C, 123I, 124I, 125I, or 131I), mass-tags including, but not limited to, stable isotopes (e.g., 13C, 2H, 17O, 18O, 15N, 19F, and 127I), positron emitting isotopes (e.g., 11C, 18F, 13N, 124I, and 15O), and fluorescent labels are signal generating reporter groups which can be detected without further modifications. Detectable moities may be analyzed by methods including, but not limited to fluorescence, positron emission tomography, SPECT medical imaging, chemiluminescence, electron-spin resonance, ultraviolet/visible absorbance spectroscopy, mass spectrometry, nuclear magnetic resonance, magnetic resonance, flow cytometry, autoradiography, scintillation counting, phosphoimaging, and electrochemical methods.

The term "chemiluminescent group," as used herein, refers to a group which emits light as a result of a chemical reaction without the addition of heat. By way of example, luminol (5-amino-2,3-dihydro-1,4-phthalazinedione) reacts with oxidants like hydrogen peroxide (H2O2) in the presence of a base and a metal catalyst to produce an excited state product (3-aminophthalate, 3-APA).

The term "chromophore," as used herein, refers to a molecule which absorbs light of visible wavelengths, UV wavelengths or IR wavelengths.

The term "dye," as used herein, refers to a soluble, coloring substance which contains a chromophore.

The term "electron dense group," as used herein, refers to a group which scatters electrons when irradiated with an electron beam. Such groups include, but are not limited to, ammonium molybdate, bismuth subnitrate, cadmium iodide, carbohydrazide, ferric chloride hexahydrate, hexamethylene tetramine, indium trichloride anhydrous, lanthanum nitrate, lead acetate trihydrate, lead citrate trihydrate, lead nitrate, periodic acid, phosphomolybdic acid, phosphotungstic acid, potassium ferricyanide, potassium ferrocyanide, ruthenium red, silver nitrate, silver proteinate (Ag Assay: 8.0-8.5%) "Strong", silver tetraphenylporphin (S-TPPS), sodium chloroaurate, sodium tungstate, thallium nitrate, thiosemicarbazide (TSC), uranyl acetate, uranyl nitrate, and vanadyl sulfate.

The term "energy transfer agent," as used herein, refers to a molecule which either donates or accepts energy from another molecule. By way of example only, fluorescence resonance energy transfer (FRET) is a dipole-dipole coupling process by which the excited-state energy of a fluorescence donor molecule is non-radiatively transferred to an unexcited acceptor molecule which then fluorescently emits the donated energy at a longer wavelength. The term "moiety incorporating a heavy atom," as used herein, refers to a group which incorporates an ion of atom which is usually heavier than carbon. In some embodiments, such ions or atoms include, but are not limited to, silicon, tungsten, gold, lead, and uranium.

The term "photoaffinity label," as used herein, refers to a label with a group, which, upon exposure to light, forms a linkage with a molecule for which the label has an affinity.

The term "photocaged moiety," as used herein, refers to a group which, upon illumination at certain wavelengths, covalently or non-covalently binds other ions or molecules.

The term "photoisomerizable moiety," as used herein, refers to a group wherein upon illumination with light changes from one isomeric form to another.

The term "radioactive moiety," as used herein, refers to a group whose nuclei spontaneously give off nuclear radiation, such as alpha, beta, or gamma particles; wherein, alpha particles are helium nuclei, beta particles are electrons, and gamma particles are high energy photons.

The term "spin label," as used herein, refers to molecules which contain an atom or a group of atoms exhibiting an unpaired electron spin (i.e. a stable paramagnetic group) that in some embodiments are detected by electron spin resonance spectroscopy and in other embodiments are attached to another molecule. Such spin-label molecules include, but are not limited to, nitryl radicals and nitroxides, and in some embodiments are single spin-labels or double spin-labels.

The term "quantum dots," as used herein, refers to colloidal semiconductor nanocrystals that in some embodiments are detected in the near-infrared and have extremely high quantum yields (i.e., very bright upon modest illumination).

One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering moiety, such as a bivalent saturated or unsaturated hydrocarbon chain. In some embodiments, detectable moieties are attached to a provided compound via click chemistry. In some embodiments, such moieties are attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, JJ, 52-57. In some embodiments, a click ready inhibitor moiety is provided and reacted with a click ready -T-R1 moiety. As used herein, "click ready" refers to a moiety containing an azide or alkyne for use in a click chemistry reaction. In some embodiments, the click ready inhibitor moiety comprises an azide. In certain embodiments, the click ready -T-R1 moiety comprises a strained cyclooctyne for use in a copper-free click chemistry reaction (for example, using methods described in Baskin et al., Proc. Natl. Acad. Sci. USA 2007, 104, 16793-16797).

Further aspects of the invention relate to using assays described herein in screening methods for therapeutics. For example, therapeutics or potential therapeutics can be added to samples within the assays described herein and the effect of the therapeutic or potential therapeutic on lipophilic or amphiphilic molecules, such as cholesterol, binding, transport or efflux can be measured.

Nanoparticles

Articles, compositions, kits, and methods relating to nanostructures, including those that can sequester molecules such as cholesterol, are provided. Certain embodiments described herein include structures having a core-shell type arrangement; for instance, a nanoparticle core may be surrounded by a shell including a material, such as a lipid bilayer, that can interact with cholesterol and/or other lipids. In some embodiments, the structures, when introduced into a subject, can sequester cholesterol and/or other lipids and remove them from circulation. Accordingly, the structures described herein may be used to diagnose, prevent, treat or manage certain diseases or bodily conditions, especially those associated with abnormal lipid levels.

Certain structures described herein can mimic circulating lipoproteins such as high density lipoprotein (HDL) and low density lipoprotein (LDL), commonly referred to as "good" and "bad" cholesterol, respectively. One function of lipoproteins is to transport cholesterol and other lipids in the body in the aqueous blood, since these molecules do not normally dissolve in the blood. Lipoproteins are also responsible for a number of important pathologic functions such as atherosclerosis. These lipoproteins, and other similar circulating particles (e.g., intermediate density lipoproteins, very low density lipoproteins, etc.), include nanostructures typically between 5 and 1000 nm. Each lipoprotein is unique with regard to its surface chemistry, size and composition. However, they also have in common an outer layer of phospholipids, an inner core of hydrophobic moieties (e.g., cholesteryl esters and triglycerides), and a surface protein that identifies individual lipoprotein species and dictates physiology.

In some embodiments described herein, a core (e.g., a gold nanoparticle) can be used as a scaffold to template and direct the synthesis of structures of well defined size, shape, and surface chemistry that are amenable to a wide variety of further surface chemistry and tailorability. For example, a bottom-up, size-specific, lipoprotein synthesis may be carried out by using a nanostructure core to support a shell including a lipid bilayer and/or other suitable components.

Articles and methods described herein involve the use of nanostructure scaffolds for controllable synthesis of structures with a high degree of reproducibility and with the potential for massive scale-up. The resulting structures may be stable in a variety of solvents, may have high in vivo circulation times, and may be relatively inexpensive to fabricate. Additionally, as lipids can be easily modified with commercially available linker chemistries, the structures described herein are amenable to further functionalization with potential pharmacological agents and/or targeting/recognition agents such as antibodies, small molecules and proteins. Further advantages are described in more detail below.

Nanostructures compatible with aspects of the invention are further described in, and incorporated by reference from PCT/US2009/002540, the content of which is incorporated by reference herein in its entirety.

In embodiments in which the core is a nanostructure, the core includes a surface to which one or more components can be optionally attached. For instance, in some cases, core is a nanostructure surrounded by shell, which includes an inner surface and an outer surface. The shell may be formed, at least in part, of one or more components, such as a plurality of lipids, which may optionally associate with one another and/or with surface of the core. For example, components may be associated with the core by being covalently attached to the core, physisorbed, chemisorbed, or attached to the core through ionic interactions, hydrophobic and/or hydrophilic interactions, electrostatic interactions, van der Waals interactions, or combinations thereof. In one particular embodiment, the core includes a gold nanostructure and the shell is attached to the core through a gold-thiol bond.

Optionally, components can be crosslinked to one another. Crosslinking of components of a shell can, for example, allow the control of transport of species into the shell, or between an area exterior to the shell and an area interior of the shell. For example, relatively high amounts of crosslinking may allow certain small, but not large, molecules to pass into or through the shell, whereas relatively low or no crosslinking can allow larger molecules to pass into or through the shell. Additionally, the components forming the shell may be in the form of a monolayer or a multilayer, which can also facilitate or impede the transport or sequestering of molecules. In one exemplary embodiment, shell includes a lipid bilayer that is arranged to sequester cholesterol, as described in more detail below.

It should be understood that a shell which surrounds a core need not completely surround the core, although such embodiments may be possible. For example, the shell may surround at least 50%, at least 60%, at least 70%, at least 80%, at least 90%, or at least 99% of the surface area of a core. In some cases, the shell substantially surrounds a core. In other cases, the shell completely surrounds a core. The components of the shell may be distributed evenly across a surface of the core in some cases, and unevenly in other cases. For example, the shell may include portions (e.g., holes) that do not include any material in some cases. If desired, the shell may be designed to allow penetration and/or transport of certain molecules and components into or out of the shell, but may prevent penetration and/or transport of other molecules and components into or out of the shell. The ability of certain molecules to penetrate and/or be transported into and/or across a shell may depend on, for example, the packing density of the components forming the shell and the chemical and physical properties of the components forming the shell. As described herein, the shell may include one layer of material, or multilayers of materials in some embodiments.

Structure may also include one or more components such as proteins, nucleic acids, and bioactive agents which may optionally impart specificity to the structure. One or more components may be associated with the core, the shell, or both; e.g., they may be associated with surface of the core, inner surface of the shell, outer surface of the shell, and/or embedded in the shell. For example, one or more components may be associated with the core, the shell, or both through covalent bonds, physisorption, chemisorption, or attached through ionic interactions, hydrophobic and/or hydrophilic interactions, electrostatic interactions, van der Waals interactions, or combinations thereof. In one particular embodiment, shell is in the form of a lipoprotein assembly or structure which includes both proteins and lipids that are covalently or non-covalently bound to one another. For example, the shell may be in the form of an apolipoprotein assembly that serves as an enzyme co-factor, receptor ligand, and/or lipid transfer carrier that regulates the uptake of lipids. As described herein, the components of structure may be chosen such that the surface of the structure mimics the general surface composition of HDL, LDL, or other structures.

It should be understood that components and configurations other than those described herein may be suitable for certain structures and compositions, and that not all of the components described are necessarily present in some embodiments.

In some cases, core is hollow and therefore does not include a nanostructure core. Thus, in some such and other embodiments, structure includes a shell that can optionally allow components (e.g., bioactive agents, cholesterol) to pass to and from core and an environment outside of the shell. In contrast to certain existing hollow structures (e.g., liposomes) which typically have a largest cross-sectional dimension of greater than about 100 nm due to the steric hindrance of the components forming the shell, structures having a hollow core (e.g., a partially or wholly hollow core) may be very small, e.g., having a largest cross-sectional dimension of less than about 100 nm, or even less than about 50 nm. For example, liposomes that include a lipid bilayer comprising phospholipids are difficult to fabricate having a size of less than 100 nm since the phospholipids become limited sterically, thus making it difficult or impossible to form bilayered hollow structures with small radii of curvature. Using the methods described herein, however, such and other structures having small radii of curvature can be formed, as provided in more detail below.

In one set of embodiments, a structure, whether including a nanostructure core or a hollow core, is constructed and arranged to sequester, transport, or exchange certain molecules to and/or from a subject or a biological sample. For instance, a structure, when introduced into a subject, may interact with one or more components in the subject such as cells, tissues, organs, particles, fluids (e.g., blood), and portions thereof. The interaction may take place, at least in part, through the shell of a structure, and may involve, for example, the exchange of materials (e.g., proteins, peptides, polypeptides, nucleic acids, nutrients) from the one or more components of the subject to a structure, and/or from a structure to the one or more components of the subject. In some such embodiments, the shell of a structure can be designed to include components with properties that allow favorable interaction (e.g., binding, adsorption, transport) with the one or more materials from the subject. For example, the shell may include components having a certain hydrophobicity, hydrophilicity, surface charge, functional group, specificity for binding, and/or density to facilitate particular interactions, as described in more detail below. In certain embodiments, one or more materials from a subject are sequestered by a structure, and a structure facilitates excretion, breakdown, and/or transport of the material. The excretion, breakdown, and/or transport of the material can lead to certain beneficial and/or therapeutic effects. As such, the structures described herein can be used for the diagnosis, prevention, treatment or management of certain diseases or bodily conditions.

In one particular set of embodiments, a structure, whether including a nanostructure core or a hollow core, is constructed and arranged to sequester cholesterol (and/or other lipids). Without wishing to be bound by theory, it is hypothesized that a structure sequesters cholesterol through hydrophobic interactions with a hydrophobic layer (e.g., a lipid bilayer) of the structure. For example, in some cases, cholesterol can bind to a surface of the structure (e.g., to the outer surface of the shell) through hydrophobic interactions. In other cases, the cholesterol can be transported from an outer surface of the shell to an inner surface of the shell and/or to the core of the structure. The cholesterol can also be imbedded in the shell, e.g., between two layers of the shell. Optionally, a structure may include one or more apolipoproteins (e.g., apoliprotein-A1), proteins, or peptides, which can facilitate the sequestering of cholesterol. A structure may also sequester cholesterol by removing cholesterol and phospholipids from a cell, or from other circulating lipoprotein species. cholesterol sequestered by a structure may be esterified enzymatically (e.g., by lecithin:acyl CoA transferase (LCAT)) to form a cholesteryl ester that may migrate towards the center of the structure. In the case of hollow core embodiments, the cholesteryl ester may accumulate in the hollow core.

Additionally, without wishing to be bound by theory, it is believed that the structures described herein can sequester cholesterol from high concentrations of cholesterol (e.g., plaques) and transfer it to the liver directly or indirectly. For example, cholesterol may be sequestered from areas of high concentrations of cholesterol (e.g., plaques) by direct efflux of cholesterol from the plaque, or any components of the plaque, into or onto the structures described herein. In some such embodiments, the cholesterol that is sequestered by the structures is transported directly to the liver by the structures. In other embodiments, other circulating lipoprotein species (e.g., LDL) may participate in cholesterol exchange. For example, in some cases, free cholesterol or esterified cholesterol is transferred from other lipoproteins to the structures described herein. In other cases, once free cholesterol or esterified cholesterol is sequestered by the structures described herein, the cholesterol can be transferred from the structures to the other lipoprotein species, which may ultimately end up in the liver. Thus, in such embodiments, the structures described herein can augment reverse cholesterol transport indirectly. Furthermore, in the case where free cholesterol or esterified cholesterol is sequestered from the structures described herein to other lipoprotein species, the structures may further sequester cholesterol from, for example, areas of high cholesterol content, plaques, circulating lipoproteins, or other physiologic sites of high cholesterol concentration. It should be understood, however, that the structures described herein may remove cholesterol and/or other molecules by other routes, such as through urine, and the invention is not limited in this respect.

Accordingly, a structures may be used in the field of cardiovascular disease for studying atherosclerosis and cholesterol transport, and, generally, to diagnose, prevent, treat or manage diseases or bodily conditions associated with abnormal lipid levels, as described in more detail below.

The amount of a molecule (e.g., cholesterol or other lipids) sequestered by a structure and/or a composition described herein may depend on, for example, the size of the structure, the biology and surface chemistry of the particle, as well as the method of administration. As such, a single structure described herein, which may be incorporated into a pharmaceutical composition or other formulation, may be able to sequester any suitable number of a particular type of molecule (e.g., lipids such as cholesterol; steroids such as estrogen, progesterone, and testosterone; bile salts, etc.) during use, e.g., at least 2, at least 5, at least 10, at least 20, at least 30, at least 50, at least 100, at least 200, at least 500, at least 1,000, at least 2,000, at least 5,000, or at least 10,000 molecules, which may depend on the size (e.g., surface area and/or volume) of the structure, the particular application, and the method of administration. In some cases, such numbers of molecules can be bound to the structure at one particular instance.

In some cases, a single structure has a binding constant for cholesterol, $K_d$, of, for example, less than or equal to about 100 μM, less than or equal to about 10 μM, less than or equal to about 1 μM, less than or equal to about 0.1 μM, less than or equal to about 10 nM, less than or equal to about 7 nM, less than or equal to about 5 nM, less than or equal to about 2 nM, less than or equal to about 1 nM, less than or equal to about 0.1 nM, less than or equal to about 10 pM, less than or equal to about 1 pM, less than or equal to about 0.1 pM, less than or equal to about 10 fM, or less than or equal to about 1 fM. Methods for determining the amount of cholesterol sequestered and binding constants are provided in more detail below.

In certain embodiments, the molecules that are sequestered by the structures described herein cause the structure to grow in size (e.g., cross-sectional area, surface area and/or volume), e.g., depending on the number of molecules sequestered. The molecules may associate with a surface of a structure, be imbedded in a shell of a structure, be transported to a core of the structure, or combinations thereof, as described herein. As such, the size of a structure (e.g., cross-sectional area, surface area and/or volume) can increase by at least 5%, at least 10%, at least 20%, at least 30%, at least 50%, at least 70%, or at least 100%, from a time prior to sequestration compared to a time after/during sequestration in some embodiments.

It should be understood, however, that while many of the embodiments herein are described in the context of sequestering cholesterol or other lipids, the invention is not limited as such and the structures, compositions, kits, and methods described herein may be used to sequester other molecules and/or to prevent, treat, or manage other diseases or bodily conditions.

A core, whether being a nanostructure core or a hollow core, may have any suitable shape and/or size. For instance, the core may be substantially spherical, non-spherical, oval, rod-shaped, pyramidal, cube-like, disk-shaped, wire-like, or irregularly shaped. The core (e.g., a nanostructure core or a hollow core) may have a largest cross-sectional dimension (or, sometimes, a smallest cross-section dimension) of, for example, less than or equal to about 500 nm, less than or equal to about 250 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. In some cases, the core has an aspect ratio of greater than about 1:1, greater than 3:1, or greater than 5:1. As used herein, "aspect ratio" refers to the ratio of a length to a width, where length and width measured perpendicular to one another, and the length refers to the longest linearly measured dimension.

In embodiments in which a core includes a nanostructure core, the nanostructure core may be formed from any suitable material. For instance, in one embodiment, a nanostructure core comprises an inorganic material. The inorganic material may include, for example, a metal (e.g., Ag, Au, Pt, Fe, Cr, Co, Ni, Cu, Zn, and other transition metals), a semiconductor (e.g., silicon, silicon compounds and alloys, cadmium selenide, cadmium sulfide, indium arsenide, and indium phosphide), or an insulator (e.g., ceramics such as silicon oxide). The inorganic material may be present in the core in any suitable amount, e.g., at least 1 wt %, 5 wt %, 10 wt %, 25 wt %, 50 wt %, 75 wt %, 90 wt %, or 99 wt %. In one embodiment, the core is formed of 100 wt % inorganic material. The nanostructure core may, in some cases, be in the form of a quantum dot, a carbon nanotube, a carbon nanowire, or a carbon nanorod. In some cases, the nanostructure core comprises, or is formed of, a material that is not of biological origin. In some embodiments, a nanostructure includes one or more organic materials such as a synthetic polymer and/or a natural polymer. Examples of synthetic polymers include non-degradable polymers such as polymethacrylate and degradable polymers such as polylactic acid, polyglycolic acid and copolymers thereof. Examples of natural polymers include hyaluronic acid, chitosan, and collagen.

A structure, which may include a shell surrounding a core, may also have any suitable shape and/or size. For instance, a structure may have a shape that is substantially spherical, oval, rod-shaped, pyramidal, cubed-like, disk-shaped, or irregularly shaped. The largest cross-sectional dimension (or, sometimes, a smallest cross-section dimension) of a structure may be, for example, less than or equal to about 500 nm, less than or equal to about 250 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. The structure may also have an aspect ratio substantially similar to the aspect ratio of the core.

Furthermore, a shell of a structure can have any suitable thickness. For example, the thickness of a shell may be at least 10 Angstroms, at least 0.1 nm, at least 1 nm, at least 2 nm, at least 5 nm, at least 7 nm, at least 10 nm, at least 15 nm, at least 20 nm, at least 30 nm, at least 50 nm, at least 100 nm, or at least 200 nm (e.g., from the inner surface to the outer surface of the shell). In some cases, the thickness of a shell is less than 200 nm, less than 100 nm, less than 50 nm, less than 30 nm, less than 20 nm, less than 15 nm, less than 10 nm, less than 7 nm, less than 5 nm, less than 3 nm, less than 2 nm, or less than 1 nm (e.g., from the inner surface to the outer surface of the shell). Such thicknesses may be determined prior to or after sequestration of molecules as described herein.

Those of ordinary skill in the art are familiar with techniques to determine sizes of structures and particles. Examples of suitable techniques include dynamic light scattering (DLS) (e.g., using a Malvern Zetasizer instrument), transmission electron microscopy, scanning electron microscopy, electroresistance counting and laser diffraction. Other suitable techniques are known to those or ordinary skill in the art. Although many methods for determining sizes of nanostructures are known, the sizes described herein (e.g., largest or smallest cross-sectional dimensions, thicknesses) refer to ones measured by dynamic light scattering.

The shell of a structure described herein may comprise any suitable material, such as a hydrophobic material, a hydrophilic material, and/or an amphiphilic material. Although the shell may include one or more inorganic materials such as those listed above for the nanostructure core, in many embodiments the shell includes an organic material such as a lipid or certain polymers. The components of the shell may be chosen, in some embodiments, to facilitate the sequestering of cholesterol or other molecules. For instance, cholesterol (or other sequestered molecules) may bind or otherwise associate with a surface of the shell, or the shell may include components that allow the cholesterol to be internalized by the structure. Cholesterol (or other sequestered molecules) may also be embedded in a shell, within a layer or between two layers forming the shell. The components of a shell may be charged, e.g., to impart a charge on the surface of the structure, or uncharged.

In one set of embodiments, a structure described herein or a portion thereof, such as a shell of a structure, includes one or more natural or synthetic lipids or lipid analogs (i.e., lipophilic molecules). One or more lipids and/or lipid analogues may form a single layer or a multi-layer (e.g., a bilayer) of a structure. In some instances where mutli-layers are formed, the natural or synthetic lipids or lipid analogs interdigitate (e.g., between different layers). Non-limiting examples of natural or synthetic lipids or lipid analogs include fatty acyls, glycerolipids, glycerophospholipids, sphingolipids, saccharolipids and polyketides (derived from condensation of ketoacyl subunits), and sterol lipids and prenol lipids (derived from condensation of isoprene subunits).

In one particular set of embodiments, a structure described herein includes one or more phospholipids. The one or more phospholipids may include, for example, phosphatidylcholine, phosphatidylglycerol, lecithin, β, γ-dipalmitoyl-α-lecithin, sphingomyelin, phosphatidylserine, phosphatidic acid, N-(2,3-di(9-(Z)-octadecenyloxy))-prop-1-yl-N,N,N-trimethylam monium chloride, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, palmitoyl-oleoyl-phosphatidylcholine, di-stearoyl-phosphatidylcholine, stearoyl-palmitoyl-phosphatidylcholine, di-palmitoyl-phosphatidylethanolamine, di-stearoyl-phosphatidylethanolamine, di-myrstoyl-phosphatidylserine, di-oleyl-phosphatidylcholine, 1,2-dipalmitoyl-sn-glycero-3-phosphothioethanol, and combinations thereof. In some cases, a shell (e.g., a bilayer) of a structure includes 50-200 natural or synthetic lipids or lipid analogs (e.g., phospholipids). For example, the shell may include less than about 500, less than about 400, less than about 300, less than about 200, or less than about 100 natural or synthetic lipids or lipid analogs (e.g., phospholipids), e.g., depending on the size of the structure.

Non-phosphorus containing lipids may also be used such as stearylamine, docecylamine, acetyl palmitate, and fatty acid amides. In other embodiments, other lipids such as fats, oils, waxes, cholesterol, sterols, fat-soluble vitamins (e.g., vitamins A, D, E and K), glycerides (e.g., monoglycerides, diglycerides, triglycerides) can be used to form portions of a structure described herein.

A portion of a structure described herein such as a shell or a surface of a nanostructure may optionally include one or more alkyl groups, e.g., an alkane-, alkene-, or alkyne-containing species, that optionally imparts hydrophobicity to the structure. An "alkyl" group refers to a saturated aliphatic group, including a straight-chain alkyl group, branched-chain alkyl group, cycloalkyl (alicyclic) group, alkyl substituted cycloalkyl group, and cycloalkyl substituted alkyl group. The alkyl group may have various carbon numbers, e.g., between $C_2$ and $C_{40}$, and in some embodiments may be greater than $C_5$, $C_{10}$, $C_{15}$, $C_{20}$, $C_{25}$, $C_{30}$, or $C_{35}$. In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, tert-butyl, cyclobutyl, hexyl, cyclohexyl, and the like.

The alkyl group may include any suitable end group, e.g., a thiol group, an amino group (e.g., an unsubstituted or substituted amine), an amide group, an imine group, a carboxyl group, or a sulfate group, which may, for example, allow attachment of a ligand to a nanostructure core directly or via a linker. For example, where inert metals are used to form a nanostructure core, the alkyl species may include a thiol group to form a metal-thiol bond. In some instances, the alkyl species includes at least a second end group. For example, the species may be bound to a hydrophilic moiety such as polyethylene glycol. In other embodiments, the second end group may be a reactive group that can covalently attach to another functional group. In some instances, the second end group can participate in a ligand/receptor interaction (e.g., biotin/streptavidin).

In some embodiments, the shell includes a polymer. For example, an amphiphilic polymer may be used. The polymer may be a diblock copolymer, a triblock copolymer, etc., e.g., where one block is a hydrophobic polymer and another block is a hydrophilic polymer. For example, the polymer may be a copolymer of an a-hydroxy acid (e.g., lactic acid) and polyethylene glycol. In some cases, a shell includes a hydrophobic polymer, such as polymers that may include certain acrylics, amides and imides, carbonates, dienes, esters, ethers, fluorocarbons, olefins, sytrenes, vinyl acetals, vinyl and vinylidene chlorides, vinyl esters, vinyl ethers and ketones, and vinylpyridine and vinylpyrrolidones polymers. In other cases, a shell includes a hydrophilic polymer, such as polymers including certain acrylics, amines, ethers, styrenes, vinyl acids, and vinyl alcohols. The polymer may be charged or uncharged. As noted herein, the particular components of the shell can be chosen so as to impart certain functionality to the structures.

Where a shell includes an amphiphilic material, the material can be arranged in any suitable manner with respect to the nanostructure core and/or with each other. For instance, the amphiphilic material may include a hydrophilic group that points towards the core and a hydrophobic group that extends away from the core, or, the amphiphilic material may include a hydrophobic group that points towards the core and a hydrophilic group that extends away from the core. Bilayers of each configuration can also be formed.

The structures described herein may also include one or more proteins, polypeptides and/or peptides (e.g., synthetic peptides, amphiphilic peptides). In one set of embodiments, the structures include proteins, polypeptides and/or peptides that can increase the rate of cholesterol transfer or the cholesterol-carrying capacity of the structures. The one or more proteins or peptides may be associated with the core (e.g., a surface of the core or embedded in the core), the shell (e.g., an inner and/or outer surface of the shell, and/or embedded in the shell), or both. Associations may include covalent or non-covalent interactions (e.g., hydrophobic and/or hydrophilic interactions, electrostatic interactions, van der Waals interactions).

An example of a suitable protein that may associate with a structure described herein is an apolipoprotein, such as apolipoprotein A (e.g., apo A-I, apo A-II, apo A-IV, and apo A-V), apolipoprotein B (e.g., apo B48 and apo B 100), apolipoprotein C (e.g., apo C-I, apo C-II, apo C-III, and apo C-IV), and apolipoproteins D, E, and H. Specifically, apo $A_1$, apo $A_2$, and apo E promote transfer of cholesterol and cholesteryl esters to the liver for metabolism and may be useful to include in structures described herein. Additionally or alternatively, a structure described herein may include one or more peptide analogues of an apolipoprotein, such as one described above. A structure may include any suitable number of, e.g., at least 1, 2, 3, 4, 5, 6, or 10, apolipoproteins or analogues thereof. In certain embodiments, a structure includes 1-6 apolipoproteins, similar to a naturally occurring HDL particle. Of course, other proteins (e.g., non-apolipoproteins) can also be included in structures described herein.

Optionally, one or more enzymes may also be associated with a structure described herein. For example, lecithin-cholesterol acyltransferase is an enzyme which converts free cholesterol into cholesteryl ester (a more hydrophobic form of cholesterol). In naturally-occurring lipoproteins (e.g., HDL and LDL), cholesteryl ester is sequestered into the core of the lipoprotein, and causes the lipoprotein to change from a disk shape to a spherical shape. Thus, structures described herein may include lecithin-cholesterol acyltransferase to mimic HDL and LDL structures. Other enzymes such as cholesteryl ester transfer protein (CETP) which transfers esterified cholesterol from HDL to LDL species may also be included.

In some cases, one or more bioactive agents are associated with a structure or a composition described herein. The one or more bioactive agents may optionally be released from the structure or composition (e.g., long-term or short-term release). Bioactive agents include molecules that affect a biological system and include, for example proteins, nucleic acids, therapeutic agents, vitamins and their derivatives, viral fractions, lipopolysaccharides, bacterial fractions and hormones. Other agents of interest may include chemotherapeutic agents.

In some embodiments, one or more nucleic acids is associated with a structure described herein. A nucleic acids includes any double strand or single strand deoxyribonucleic acid (DNA) or ribonucleic acid (RNA) of variable length. Nucleic acids include sense and anti-sense strands. Nucleic acid analogs such as phosphorothioates, phosphoramidates, phosphonates analogs are also considered nucleic acids and may be used. Nucleic acids also include chromosomes and chromosomal fragments.

One or more sugar residues can optionally be associated with structures described herein.

It should be understood that the components described herein, such as the lipids, phospholipids, alkyl groups, polymers, proteins, polypeptides, peptides, enzymes, bioactive agents, nucleic acids, and species for targeting described above, may be associated with a structure in any suitable manner and with any suitable portion of the structure, e.g., the core, the shell, or both. For example, one or more such components may be associated with a surface of a core, an interior of a core, an inner surface of a shell, an outer surface of a shell, and/or embedded in a shell. Furthermore, such components can be used, in some embodiments, to facilitate the sequestration, exchange and/or transport of materials (e.g., proteins, peptides, polypeptides, nucleic acids, nutrients) from one or more components of a subject (e.g., cells, tissues, organs, particles, fluids (e.g., blood), and portions thereof) to a structure described herein, and/or from the structure to the one or more components of the subject. In some cases, the components have chemical and/or physical properties that allow favorable interaction (e.g., binding, adsorption, transport) with the one or more materials from the subject.

Additionally, the components described herein, such as the lipids, phospholipids, alkyl groups, polymers, proteins, polypeptides, peptides, enzymes, bioactive agents, and nucleic acids, may be associated with a structure described herein prior to administration to a biological sample and/or after administration to a biological sample. For example, in some cases a structure described herein includes a core and a shell which is administered, and the structure has a greater therapeutic effect after sequestering one or more components (e.g., an apolipoprotein) from a biological sample. That is, the structure may use natural components from the biological sample to increase efficacy of the structure after it has been administered.

In one aspect, methods of making structures described herein are provided. In some embodiments, methods include providing a fluid comprising a plurality of nanostructures (e.g., nanostructure cores) and a first solvent, as well as a fluid comprising a plurality of components and a second solvent. First solvent may be chosen such that it stabilizes nanostructures, preventing the nanostructures from precipitating out of solution. Second solvent may be chosen so as to solubilize components. The first and second solvents may be miscible in some embodiments, and immiscible in other embodiments. In certain embodiments in which solvents and are miscible with one another, the solvents may also be miscible with water. Such and other solvents may be useful in a single-phase synthesis. Solvents that are miscible or slightly miscible with water are known to those or ordinary skill in the art and include, for example, alcohols (e.g., ethanol, propanol), THF, DMF and DMSO. Organic solvents that are immiscible with water can also be used (e.g., in two-phase synthesis).

When components are combined with nanostructures, a shell comprising components is formed on the surface. The shell can include a monolayer of components, however, in other embodiments, multi-layers can be formed (e.g., at least two or at least three layers). If additional components are desired, the components can be combined and the components may associate with at least a portion of shell. For example, a second component present in a third solvent may be combined with nanostructure to form a structure including a shell in the form of a bilayer. The bilayer may form due to favorable interaction between components, which may be the same or different. In certain embodiments, components interdigitate.

Optionally, all or a portion of nanostructure may be removed from an assembled structure to form a partially or wholly hollow core. Nanostructure can be removed from the structure by a variety of methods, which may depend on the particular material used to form nanostructure. For instance, where nanostructure is a metal (e.g., gold) nanoparticle, solvents that are known to dissolve certain metals, such as iodine, potassium cyanide, and strong acids (e.g., nitric acid), can be used to remove the nanostructure core. Accordingly, in some cases where the core is formed of a metal (e.g., Au(0)), removal of the metal may include oxidizing the metal to form a metal salt, e.g., Au(0) to $Au^+$ and/or $Au^{3+}$. Electrochemical and redox methods can also be used to remove all or portions of a core. In some cases, a portion, but not all of the nanostructure core is removed, e.g., such that the nanostructure core is now more porous than before the removal step. In other cases, the core is released from the shell without removing a portion of the core. For example, a shell that is bonded to a metal core via sulfur-metal bonds can be released from the core by using small molecules such as dithiothreitol (DTT), which can displace the bonds. A suitable solvent or a chemical may be chosen such that it can remove at least portions of a core material, and/or release the shell from the core, without negatively affecting the shape and/or configuration of the shell, and/or degrade (e.g., denature) the components of the shell.

In certain embodiments, components are cross linked with one another prior to removing all or a portion of the nanostructure core. For example, components may be thiolated ligands which cross link by forming disulfide bonds. Any suitable method for cross linking can be used, such as photo cross linking, chemical cross linking, and oxidation-reduction methods, as known to those of ordinary skill in the art. The cross linking step may help to stabilize shell in the same or a similar configuration as that achieved when associated with nanostructure. In certain embodiments, cross linking of components is performed at the same time as the removal of nanostructure to form a partially or wholly hollow structure.

A similar approach for removing all or a portion of nanostructure can be used to form structure, which includes a shell comprising a bilayer of components surrounding a hollow core.

In some cases, instead of forming multiple layers of components on a nanostructure surface in separate steps, multi-layers can be formed in a single step. For instance, components may be combined in a single phase of a liquid, e.g., a liquid that solubilizes and/or stabilizes the components and the nanostructures. Such a liquid may, in some cases, comprise water, or a solvent that is miscible with water. In some such embodiments, at least a first layer including components and a second layer including components are formed by self-assembly. The first and second layers in such a process may, in some instances, be formed substantially simultaneously. Additional layers can also be formed by such a process. Each of the layers can include a single component, or mixtures of components. To facilitate formation of the layers, a portion of the liquid may be removed from the mixture, e.g., by applying heat to evaporate a solvent having a low boiling point.

The ratio of components and nanostructures can be tailored depending on, for example, the type of components and nanostructures, the solvent(s) used, and the method of fabrication of the structures. For instance, to obtain solubility in aqueous solution, a suitable ratio can be chosen such that there is an ample amount of a component on the surface of the nanostructure so as to maintain water solubility. Thus, in certain instances, if the concentration of a component is too low, the structures will not be stable. Furthermore, if the ratio is too high with certain components, certain undesirable structures may be formed instead of stable monodisperse structures. Those of ordinary skill in the art can determine suitable ratios by simple experimentation in combination with the description provided herein.

Furthermore, additional components such as proteins, nucleic acids, polymers, bioactive agents (e.g., cholesterol lowering agents) or other structures can be associated with the structures at any step. For example, in some embodiments additional structures are added at the same time as addition of components, prior to the addition of components, or after the addition of components.

Advantageously, using the methods described herein, liposome-like structures having a hollow core (or at least a partially hollow core) can be formed in a size range that is unique to certain existing liposomes. For example, for many existing liposomes formed from a phospholipid bilayer and having a hollow core, the liposomes are large enough (e.g., typically greater than about 100 nm in diameter) such that the phospholipid bilayer is capable of being formed. As one attempts to make liposomes of smaller diameter, the packing of phospholipid moieties becomes limited sterically thus making it difficult or impossible to form bilayered liposomal structures with small radii of curvature (e.g., smaller than about 100 nm in diameter). Methods described herein, however, can be used to form structures of smaller diameter (e.g., structures having a largest cross-sectional dimension of less than about 100 nm, or less than or equal to about 50 nm), since the use of a nanostructure core as a template allows the arrangement of components in a shell that is dictated, at least in part, by the size and shape of the nanostructure core. Such methods can be used to make biologically relevant structures having a surface chemistry that mimics certain molecules such as HDL and LDL.

Additionally, because structures described herein can be formed by the use of nanostructures that serve as a template, and because certain nanostructures can be provided (e.g., made or purchased) having relatively high uniformity in size, shape, and mass, the structures described herein may also have relatively high uniformity in size, shape, and mass. That is, a mixture of relatively uniform structures can be formed, where the plurality of structures have a distribution of cross-sectional dimensions such that no more than about 20%, 15%, 10%, or 5% of the structures have a cross-sectional dimension greater than about 20%, 15%, 10%, or 5% of the average cross-sectional dimension. Structures having relatively high uniformity are useful in certain compositions and methods described herein.

Furthermore, the structures that are formed using methods described herein may disperse in a liquid, instead of forming aggregates. Dispersions of structures described herein are useful in certain compositions and methods described herein.

Those of ordinary skill in the art can choose appropriate components, such as those cited in, and incorporated by reference, from PCT/US2009/002540, nanostructure cores, and solvents useful for the formation of structures described herein by, for example, knowing the particular components and nanostructure cores that would lead to favorable structures, the physical properties of the components, nanostructures and solvents, and/or by a simple screening test. One simple screening test may include adding components (and/or nanostructures) to a solvent and determining whether the component (or nanostructure) is soluble or stabilized in the solvent and/or reacts with or is negatively affected by the solvent. Other simple tests can be conducted by those of ordinary skill in the art.

In one set of embodiments, the structures, compositions and methods described herein are used to diagnose, prevent, treat or manage diseases or bodily conditions associated with abnormal lipid levels. For instance, high density lipoprotein is a dynamic serum nanostructure protective against the development of atherosclerosis and resultant illnesses such as heart disease and stroke. Furthermore, in certain embodiments, diagnosis, prevention, treatment or management of diseases or bodily conditions associated with abnormal lipid levels may involve using the structures, compositions and methods described herein.

Other diseases or bodily conditions associated with abnormal lipid levels which could benefit from methods and/or compositions described herein include, for example, atherosclerosis, phlebosclerosis or any venous condition in which deposits of plaques containing cholesterol or other material are formed within the intima or inner media of veins, acute coronary syndromes, angina including, stable angina, unstable angina, inflammation, sepsis, vascular inflammation, dermal inflammation, congestive heart failure, coronary heart disease (CHD), ventricular arrythmias, peripheral vascular disease, myocardial infarction, onset of fatal myocardial infarction, non-fatal myocardial infarction, ischemia, cardiovascular ischemia, transient ischemic attacks, ischemia unrelated to cardiovascular disease, ischemia-reperfusion injury, decreased need for revascularization, coagulation disorders, thrombocytopenia, deep vein thrombosis, pancreatitis, non-alcoholic steatohepatitis, diabetic neuropathy, retinopathy, painful diabetic neuropathy, claudication, psoriasis, critical limb ischemia, impotence, dyslipidemia, hyperlipidemia, hyperlipoproteinemia, hypoalphalipoproteinemia, hypertriglyceridemia, any stenotic condition leading to ischemic pathology, obesity, diabetes including both Type I and Type II, ichtyosis, stroke, vulnerable plaques, lower-limb ulceration, severe coronary ischemia, lymphomas, cataracts, endothelial dysfunction, xanthomas, end organ dysfunction, vascular disease, vascular disease that results from smoking and diabetes, carotid and coronary artery disease, regress and shrink established plaques, unstable plaques, vessel intima that is weak, unstable vessel intima, endothelial injury, endothelial damage as a result of surgical procedures, morbidity associated with vascular disease, ulcerations in the arterial lumen, restenosis as a result of balloon angioplasty, protein storage diseases (e.g., Alzheimer's disease, prion disease), diseases of hemostasis (e.g., thrombosis, thrombophilia, disseminated intravascular coagulation, thrombocytopenia, heparin induced thrombocytopenia, thrombotic thrombocytopenic purpura,), rheumatic diseases (e.g., multiple sclerosis, systemic lupus erythematosis, sjogren's syndrome, polymyositis/dermatomyositis, scleroderma), neuroligical diseases (e.g., Parkinson's disease, Alzheimer's disease), and subindications thereof.

Further non-limiting examples of conditions associated with cholesterol levels include: Abetalipoproteinemia, Familial Dysbetalipoproteinemia, Familial Lecithin cholesterol Acyltransferase Deficiency, Familial lipoprotein Lipase Deficiency, Hyperlipoproteinemias, Hypolipidemia, Tangier Disease, Alzheimers, coronary sclerosis, high blood pressure, macular degeneration, mixed dyslipidemia, primary hypercholesterolemia In some embodiments, the disease or bodily condition is a metabolic and/or degenerative disease. Several non-limiting examples include: Alzheimer's disease, amyotrophic lateral sclerosis, amyotrophic lateral sclerosis (ALS), angina pectoris, arginase deficiency, atherosclerosis, cachexia, cancer, carbamylphosphate synthase deficiency, carboxylase defects, cataracts, chronic obstructive pulmonary disease, chronic traumatic encephalopathy, citrullinaemia, congenital heart disease, congenital lactic acidosis, congenital myopathy, coronary artery disease, coronary heart disease, crginosuccinic aciduria, cystinosis, diabetes, diabetic nephropathy, diabetic neuropathy, diabetic retinopathy, dilated cardiomyopathy, erectile dysfunction, essential tremor, facioscapulohumeral muscular dystrophy, familial cardiomyopathy, Friedreich's ataxia, galactosemia, Gierke's disease, glomerulosclerosis, glutaric acidemia type I & II, glutaric aciduria type I, glycogenosis or dextrinosis, GSD type II (acid maltase deficiency—Pompe's disease), GSD type III (glycogen debrancher deficiency—Cori's disease or Forbe's disease), GSD type IV (glycogen branching enzyme deficiency—Andersen disease), GSD type V (muscle glycogen phosphorylase deficiency—McArdle disease), GSD type VI (liver phosphorylase deficiency—Hers's disease), GSD type VII (muscle phosphofructokinase deficiency—Tarui's disease), GSD type XI (glucose transporter deficiency—Fanconi-Bickel disease), heart disease, homocystinuria, Huntington's disease, hyperinsulinemia, hyperlipidemia, hypertrophic cardiomyopathy, impaired glucose metabolism, inflammatory bowel disease (IBD), isovaleric acidemia, keratoconus, lactic acidosis (pyruvate dehydrogenase complex defects), Lewy body disease, macular degeneration, maple syrup urine disease, medium chain acyl CoA dehydrogenase (MCAD) deficiency, methylmalonic acidemia, mitochondrial myopathies, mitochondrial myopathy, mitochondrial respiratory chain defects, multiple system atrophy, muscle wasting syndrome, myotonic muscular dystrophy, n-acetyl glutamate synthetase deficiency, Niemann-Pick disease, non-ketotic hyperglycinaemia, ornithine carbamyl transferase deficiency, osteoarthritis, osteoporosis, Parkinson's disease, phenylketonuria, premenstrual syndrome, progressive supranuclear palsy, propionic acidemia, prostatitis, restrictive cardiomyopathy, rheumatic heart disease, rheumatoid arthritis, sarcopenia, spinal muscular atrophy, Tay-Sachs disease, type 2 diabetes, tyrosinaemia (Type I), ulcerative colitis, vascular restenosis, coronary heart disease.

In one particular embodiment, structures, compositions and methods described herein are used for assessing a subject's risk for atherosclerosis. In some embodiments, assays described herein can also be used to screen for agents to treat atherosclerosis. Treating atherosclerosis may include performing a therapeutic intervention that results in reducing the cholesterol content of at least one atherosclerotic plaque, or prophylactically inhibiting or preventing the formation or expansion of an atherosclerotic plaque. Generally, the volume of the atherosclerotic plaque, and hence the degree of obstruction of the vascular lumen, will also be reduced. The present structures, compositions and methods are particularly useful for treating atherosclerotic lesions associated with familial hyperlipidemias.

Treatment of atherosclerosis may reduce the cholesterol content of atherosclerotic plaques and/or the volume of atherosclerotic plaques. The cholesterol content may be reduced by, for example, at least 10%-30%, at least 30%-50%, and in some instances at least 50%-85% or more. The volume of the atherosclerotic plaques may also be reduced. The reduction in plaque volume may be, for example, at least 5%-30%, often as much as 50%, and in some instances 75% or more. Methods of determining the reduction of cholesterol content of atherosclerotic plaques and/or the volume of atherosclerotic plaques are known to those of ordinary skill in the art, and include intravascular ultrasound and magnetic resonance imaging.

In another embodiment, structures, compositions and methods described herein are used for assessing a subject's risk of having a vascular or a cardiovascular condition or assessing whether the subject is at risk of developing a cardiovascular condition. Vascular conditions are conditions that involve the blood vessels (arteries and veins). Cardiovascular conditions are conditions that involve the heart and the blood vessels associated with the heart. Examples of vascular conditions include diabetic retinopathy, diabetic nephropathy, renal fibrosis, hypertension, atherosclerosis, arteriosclerosis, atherosclerotic plaque, atherosclerotic plaque rupture, cerebrovascular accident (stroke), transient ischemic attack (TIA), peripheral artery disease, arterial occlusive disease, vascular aneurysm, ischemia, ischemic ulcer, heart valve stenosis, heart valve regurgitation and intermittent claudication. Examples of cardiovascular conditions include coronary artery disease, ischemic cardiomyopathy, myocardial ischemia, and ischemic or post-myocardial ischemia revascularization.

Structures, compositions and methods described herein can also be used for assessing a subject's risk of developing a cardiovascular condition. The degree of risk of a cardiovascular condition depends on the multitude and the severity or the magnitude of the risk factors that the subject has. Risk charts and prediction algorithms are available for assessing the risk of cardiovascular conditions in a human subject based on the presence and severity of risk factors. One commonly used algorithm for assessing the risk of a cardiovascular condition in a human subject based on the presence and severity of risk factors is the Framingham Heart Study risk prediction score. A human subject is at an elevated risk of having a cardiovascular condition if the subject's 10-year calculated Framingham Heart Study risk score is greater than 10%. Another method for assessing the risk of a cardiovascular event in a human subject is a global risk score that incorporates a measurement of a level of a marker of systemic inflammation, such as CRP, into the Framingham Heart Study risk prediction score. Other methods of assessing the risk of a cardiovascular event in a human subject include coronary calcium scanning, cardiac magnetic resonance imaging, and/or magnetic resonance angiography.

The structures, compositions and methods described herein may also be useful for prophylactic treatments.

Hyperlipidemias may also be assessed by the compositions and methods described herein.

In certain embodiments, structures and compositions described herein are used in a method involving the determination of a disease or condition of a subject or biological sample. For instance, a method may include introducing a composition comprising a plurality of structures described herein to a biological sample (e.g., in vitro), and exposing the plurality of nanostructures and/or the subject or biological sample to testing conditions that can determine a disease or condition of the subject or biological sample.

It should be understood that any suitable structures described herein can be used in such methods, including, for example, structures having a nanostructure core comprising an inorganic material and a shell substantially surrounding and attached to the nanostructure core. In some cases, such structures are adapted to sequester cholesterol. In other cases, the structures are a marker for a disease or bodily condition.

In other embodiments, a composition is introduced to a subject or a biological sample, and the structures of the composition and/or the subject or biological sample are exposed to assay conditions that can determine a disease or condition of the subject or biological sample. At least a portion of the structures may be retrieved from the subject or biological sample and an assay may be performed with the structures retrieved. The structures may be assayed for the amount and/or type of molecules bound to or otherwise sequestered by the structures. For example, in one set of embodiments, a competition assay is performed, e.g., where labeled cholesterol is added and displacement of cholesterol is monitored. The more measured uptake of labeled cholesterol, the less bound un-labeled free cholesterol is present. This can be done, for example, after a composition comprising the structures described herein are administered to a subject or a biological sample, and the structures are subsequently retrieved from the subject or biological sample. This method can be used, for example, where the structures are to be used as a diagnostic agent to see how much cholesterol (unlabeled) it has sequestered in a subject or biological sample.

Other methods can also be used to determine the amount of cholesterol sequestered by structures described herein. In some cases, labeled cholesterol (e.g., fluorescently-labeled cholesterol such as NBD-cholesterol, BODIPY-cholesterol or radioactive cholesterol) can be used. Labeled cholesterol can be added to the structures either in vivo or in vitro. By adding structures without labeled cholesterol and measuring the fluorescence increase upon binding, one can calculate the binding constant of labeled cholesterol to the structure. In addition, to remove the cholesterol from the structure, one can dissolve the particle (e.g., KCN) and then measure the resultant fluorescence in solution. Comparing to standard curve can allow determination of the number of cholesterol molecules per particle. Other methods such as organic extraction and quantitative mass spectrometry can also be used to calculate amount of cholesterol sequestered by one or more structures described herein.

Further aspects of the invention relate to kits for measuring binding between a cholesterol acceptor and cholesterol. Kits can comprise one or more types of fluorescently labeled cholesterol analogs and one or more types of lapidated gold nanoparticles. Kits can further comprise instructions for use.

The kits described herein may also contain one or more containers, which can contain components such as the structures, signaling entities, and/or biomolecules as described. The kits also may contain instructions for mixing, diluting, and/or administrating the compounds. The kits also can include other containers with one or more solvents, surfactants, preservatives, and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are used, the liquid form may be concentrated or ready to use. The solvent will depend on the particular inventive structure and the mode of use or administration. Suitable solvents for compositions are well known and are available in the literature.

The kit, in one set of embodiments, may comprise one or more containers such as vials, tubes, and the like, each of the containers comprising one of the separate elements to be used in the method. For example, one of the containers may comprise a positive control in the assay. Additionally, the kit may include containers for other components, for example, buffers useful in the assay.

As used herein, a "subject" or a "patient" refers to any mammal (e.g., a human), for example, a mammal that may be susceptible to a disease or bodily condition such as a disease or bodily condition associated with abnormal lipid levels. Examples of subjects or patients include a human, a non-human primate, a cow, a horse, a pig, a sheep, a goat, a dog, a cat or a rodent such as a mouse, a rat, a hamster, or a guinea pig. Generally, the invention is directed toward use with humans. A subject may be a subject diagnosed with a certain disease or bodily condition or otherwise known to have a disease or bodily condition. In some embodiments, a subject may be diagnosed as, or known to be, at risk of developing a disease or bodily condition. In some embodiments, a subject may be diagnosed with, or otherwise known to have, a disease or bodily condition associated with abnormal lipid levels, as described herein. In certain embodiments, a subject may be selected for diagnosis and/or treatment on the basis of a known disease or bodily condition in the subject. In some embodiments, a subject may be selected for diagnosis and/or treatment on the basis of a suspected disease or bodily condition in the subject. In some embodiments, the presence of an existing disease or bodily condition may be suspected, but not yet identified in a subject.

A "biological sample," as used herein, is any cell, body tissue, or body fluid sample obtained from a subject. Non-limiting examples of body fluids include, for example, lymph, saliva, blood, urine, and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods.

The following examples are intended to illustrate certain embodiments of the present invention, but are not to be construed as limiting and do not exemplify the full scope of the invention.

EXAMPLES

Example 1

Development of a Cell-free Competition Assay to Measure the Dissociation Constant of Cholesterol and Human Serum Using a Biomimetic Nanostructure Introduction Reverse Cholesterol Transport (RCT) is a major function of high density lipoproteins and may protect against atherosclerosis. Measurement of cellular RCT improves assessment of cardiovascular risk, but current methods of measurement are limited in clinical applicability. Here, a rapid, cell-free competition assay to measure the dissociation constant of human serum for cholesterol is described using a fluorescently labeled cholesterol analog and a biomimetic lipidated gold nanoparticle. Using this assay, the $K_D$ of human serum as well as a high density lipoprotein-enriched fraction of serum is reported. Because cholesterol binding to serum cholesterol acceptors is a significant step in cellular RCT, this assay has widespread applications for assessing cardiovascular risk.

An intriguing property of colloidal gold is that it has the ability to quench fluorescent signals when the fluorescent moeity is in close physical proximity to the gold nanoparticle. Boron-dipyrromethene (BODIPY)-labelled cholesterol is a highly fluorescent molecule which we show (vide infra) to be strongly quenched by AuNP-HDL in a dose-dependent and titratable manner. Using assays described herein, it was found that BODIPY-Cholesterol is reversibly bound to AuNP-HDL, and that the addition of a cholesterol acceptor, (such as ApoB-depleted human serum, which contains HDL) leads to recovery of the fluorescent signal in a dose-dependent manner. Furthermore, because of the stability of the fluorescent signal, using this method, the binding capacity and kinetics of cholesterol binding to both HDL-AuNP and the competitive natural cholesterol acceptor can be ascertained. An effective $K_D$ of the cholesterol acceptor added, such as human serum, can also be calculated. These parameters are fundamental biochemical parameters that are highly related to the process of reverse cholesterol transport. Measuring these functional parameters in a clinical test is very useful in determining a patient's functional capacity for reverse cholesterol transport.

Materials and Methods

Synthesis of Lipidated Nanoparticles

Citrate-stabilized colloidal gold nanoparticles at 5 nm diameter and 80 nM concentration were purchased from Ted Pella, Redding, Calif. Phospholipids were purchased from Avanti Polar Lipids, Alabaster, Alabama, and 1 mM stock solutions of each were made. 100% Ethanol (Sigma Aldrich, St. Louis, Mo.) as well as lipid stocks were added to the gold nanoparticle such that the final concentration of ethanol was 20%, the colloidal gold was 64 nM, and 250-fold excesses of each lipid were present. After a two hour room temperature incubation, the solutions were purified by diafiltration with a KrosFlo Research II tangential flow filtration system (Spectrum Laboratories, Rancho Dominguez, Calif.). The samples were first concentrated down to a minimum holdup volume of approximately 5 ml, and were then exchanged with buffer (Ultrapure 18.2 MΩ water) continuously for at least 7 volumes (35 ml) to remove excess lipid. Concentration of the samples was then assessed by absorbance spectroscopy, using the extinction coefficient of 5 nm gold colloid of $9.696 \times 10^6$. Prior to use in further experiments the lipidated nanoparticle stock was diluted with ultrapure water to a final concentration of 1.0 µM.

In some embodiments, HDL AuNP constructs were synthesized as follows. Briefly, an 80 nM solution of 5 nm colloidal gold was incubated with a five-fold molar excess of purified ApoA1 protein. Next 250-fold molar excess of 1,2-dipalmitoyl-sn-glycero-3-phosphoethanolamine-N-(3-(2-pyridyldithio)proprionate (PDP PE) and 1,2-dipalmitoyl-sn-glycero-3-phosphocholine (DPPC) lipids were added and incubated with the ApoA1-Gold Nanoparticle for 2 hours in 20% Ethanol. Finally, excess reagents and ethanol were purified from the particles using a tangential flow filtration system, resulting in stable HDL AuNPs in water. The concentration of these particles was then determined using absorbance at 525 nM, the absorption maximum for 5 nm colloidal gold.

Fluorescence Measurements

All fluorescence measurements were made using black 96-well plates (Costar, Tewksbury, Mass.) on a BioTek Synergy 2 plate reading fluorometer (Winooski, VT) using read settings as follows: Tungsten lamp; Excitation filter: 485/20 nm; Emission filter: 528/20 nm; Optics position: Top read 510 nm; Sensitivity: 100. All reactions were carried out in a total volume of 200 µl of water at 37° C. BODIPY Cholesterol stock solution used in these experiments was 125 µM in 100% Ethanol. Stock solution was made stored at −20° C.; working stocks were made fresh by diluting a portion of the stock solution to 1.25 µM or 2.5 µM in water. Serum samples used in this experiment were collected in compliance with Institutional guidelines for human subjects research.

Cellular RCT Assay

A cellular RCT assay was performed by plating J774 mouse macrophages (ATCC, Bethesda, Md.) on day 1, labeling the cells with $^3$H-Cholesterol on day 2, upregulating membrane cholesterol transport proteins with a cyclic AMP analog on day 3, and incubating for 4 hours the radiolabeled cells with a cholesterol acceptor solution, such as human serum, on day 4.[3,4] Percent efflux was calculated as specific radioactivity in the serum-containing media divided by total radioactivity in the cells and the media.

Increased percent efflux to ApoB-depleted serum (vide infra), a serum fraction relatively enriched in HDL,[4] associates with coronary disease status even after adjusting for total amount of HDL.[3] Thus, quantifying the function of HDL independent of HDL concentration leads to improved diagnostics. The cellular RCT assay may be conceptualized as being dependent upon both cellular interactions with lipoproteins, and lipoprotein interactions with cholesterol itself. Importantly, data demonstrate the cell-independent component contributes most to overall efflux.[5] The method herein demonstrated, allows measurement of cholesterol binding with serum cholesterol acceptors, independent of the cellular context, and provides a means to calculate $K_D$ values.

In some embodiments, the RCT assay was performed as follows: A 250 uM stock solution of BODIPY-Cholesterol in 100% Ethanol was created. 5 ul of BODIPY stock solution was added to a well of a 96-well plate suitable for fluorescence measurements. 15 ul of Ethanol and 80 ul of water were added. Baseline fluorescence was then recorded using a plate-reading fluorometer using the excitation and emission filters of 485/20 and 528/20, respectively. 100 ul of HDL AuNP at a concentration of 500 nM was then added and fluorescence was recorded at 2 minute intervals for 30 minutes. An approximately 70% decline in fluorescence was observed owing to quenching of BODIPY-Cholesterol signal upon binding of the molecule to the HDL-AuNP construct. A volume of approximately 20 ul of cholesterol acceptor, such as purified ApoA1, Human HDL, or ApoB-depleted human serum, was added and fluorescence was recorded at 2 minute intervals for 60 minutes. Depending on the amount and capacity of the cholesterol acceptor added, fluorescence recovery was observed as the new (non-quenching) cholesterol acceptor competes for BODIPY-Cholesterol bound to and quenched by the HDL-AuNP construct. The amount of fluorescence recovery for a given cholesterol acceptor monotonically increased as a function of the concentration of that acceptor (FIG. 1).

Preparation of ApoB-depleted serum was completed as follows. Polyethylene glycol with an average molecular weight of 8000 (PEG 8000) was prepared as a 20% weight/volume solution in 200 mM glycine, pH 7.4. Serum and PEG solution were mixed in a 10:4 ratio and incubated at room temperature for 20 minutes, then centrifuged at 12,700×g for 30 minutes at 4 degrees Celsius to pellet the ApoB fraction. The supernatant was essentially free of ApoB containing lipoproteins, including low density lipoprotein (LDL), and was therefore relatively enriched in HDL, free Apo A1, and albumin, all of which are capable of binding cholesterol.

This assay technology may exquisitely calculate the ability of human serum cholesterol acceptors (e.g. Apo A1, HDLs) to efflux cholesterol in a non-radioactive and non-cell based assay. Furthermore, the assay can be automated, scaled, is inexpensive, rapid, and easy. There are no comparable tests on the market.

Results and Discussion

Methods described herein are based on a fluorescence-based competition assay that harnesses the quenching capacity of the gold core of a biomimetic lipid construct to measure the $K_D$ of cholesterol from serum and fractions thereof. Data presented herein demonstrate that this assay is capable of rapidly and quantitatively measuring cholesterol binding to biomimetic nanostructures. Using assays developed herein, interrogation of cholesterol binding to complex biological matrices (e.g., human serum and serum HDL fractions) is quantitative, rapid, and can be automated for high-throughput screening. Finally, the assay can be easily adapted for applications where cholesterol binding, transport, or metabolism (or other similar fluorescently-tagged analytes), is of interest.

Figure 4:
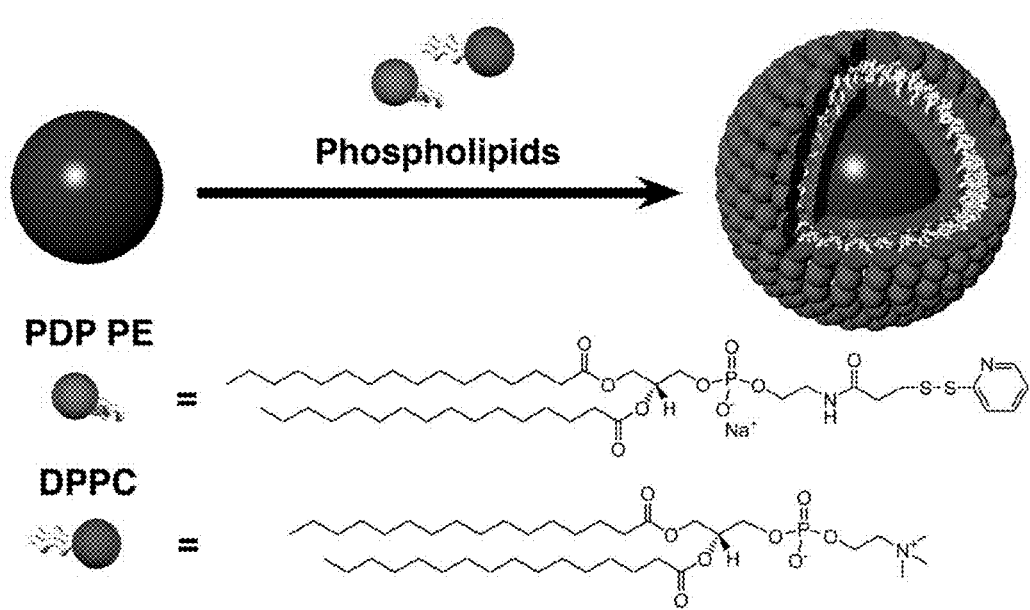
FIG. 4 shows an illustration of lipidated nanoparticles synthesis.

In order to study cholesterol binding, lipidated nanoparticles (NPs) were synthesized using a 5 nm diameter gold nanoparticle template core (FIG. 4).[7] Gold nanoparticles (Ted Pella, 80 nM) were incubated with a 250-fold excess each of 1,2-dipalmitoyl-sn-glycero-3-phosphoethanolamine-N-[3-(2-pyridyldithio)propionate] (PDP PE) and 1,2-dipalmitoyl-sn-glycero-3-phosphocholine (DPPC) in 20% ethanol (v/v). Incubation took place for two hours at room temperature. The NP conjugates were purified from unreacted lipids by using tangential flow filtration (Spectrum Laboratories, Rancho Dominguez, Calif.). Conjugates were characterized as previously described.[7]

To measure cholesterol binding, NPs were titrated into a solution with 250 nM of fluorescent cholesterol analog, 23-(dipyrrometheneboron difluoride)-24-norCholesterol (BODIPY-Cholesterol, Ex: 495 nm, Em: 507 nm). Fluorescence quenching was measured as the BODIPY-Cholesterol bound to the surface of the NPs. Binding was modeled as a receptor (NP) with multiple binding sites ($n_{NP,chol}$) with identical dissociation constants ($K_{D,NP}$). Binding isotherms were fit to the quadratic form of the binding equilibrium[11] (Equation 1) using non-linear least-squares regression to estimate the parameters $K_{D,NP}$ and $n_{NP,chol}$:

$$[Chol]_f = \frac{-(n_{NP,Chol} + K_{D,NP} - [Chol]_T) + \sqrt{(n_{NP,Chol}[NP] + K_{D,NP} - [Chol]_T) + 4K_D - [Chol]_T}}{2}$$

Figure 2:
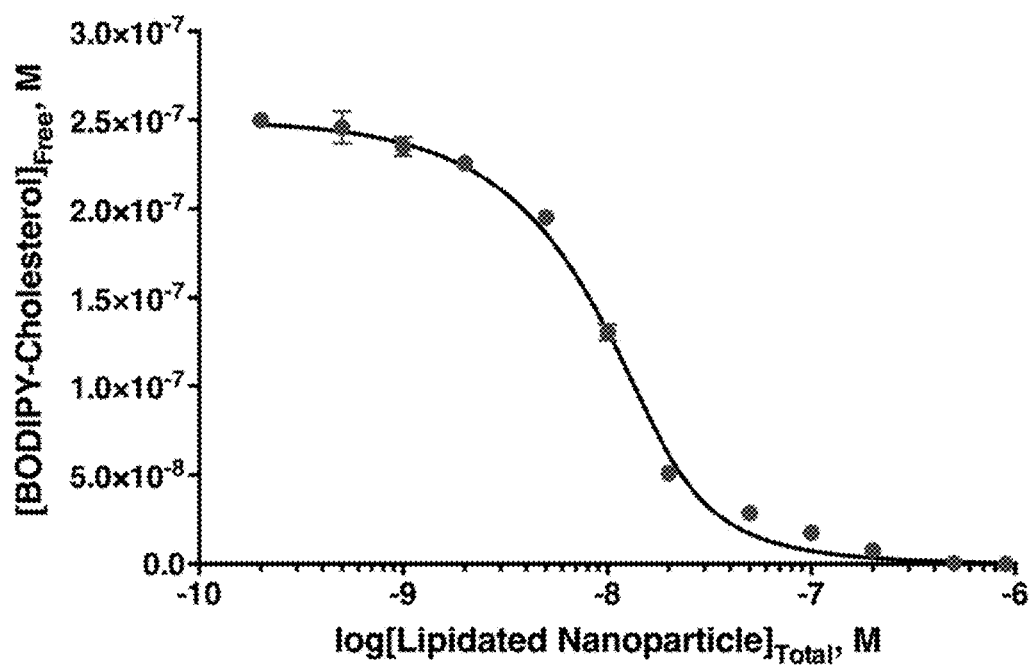
FIG. 2 shows a lipidated nanoparticle templated with 5 nm diameter gold which was titrated into 250 nM of fluorescent BODIPY-Cholesterol. Fluorescence quenching was measured upon binding. Nonlinear regression analysis modeling the BODIPY-Cholesterol interaction with the lipidated nanoparticle as a multiple binding site interaction with same $K_D$ and no cooperativity yields a $K_D$ of 40±9 nM and a binding site number of 16±1 binding sites. Error bars denote standard deviations of technical quadruplicates.

Equation 1

Where $[Chol]_f$ is the free concentration of BODIPY-Cholesterol and $[Chol]_T$ is the total concentration of BODIPY-Cholesterol. The Klotz plot is shown in FIG. 2; regression analysis demonstrated the $K_{D,NP}$ for NP-Cholesterol was 40±9 nM, while $n_{NP,chol}$ was 16±1. These values favorably correspond to those reported for similar NPs.[7]

To determine the effective $K_D$ of serum ($K_{D,serum}$) for cholesterol, competition assays between NP and serum fractions were performed. Two types of serum fraction were tested: (1) whole serum, and (2) ApoB-depleted serum. ApoB-depleted serum was prepared by incubation of serum in a 10:4 ratio with a solution of 20% w/v polyethylene glycol at a MW of 8000 and 200 mM glycine, pH 7.4 for 20 minutes at room temperature, followed by centrifugation at 12,800×g for 30 minutes at 4° C. This leaves a serum supernatant depleted of LDL particles, and enriched in HDL particles, lipid poor ApoA1, and albumin, a relevant fraction for assessing reverse cholesterol transport.[3]

Equation 2 gives a standard form of the competition equilibrium relating $K_{D,serum}$ to $EC_{50}$:

$$K_{D,Serum} = \frac{K_{D,NP}}{n_{NP,Chol}[NP]} \times EC_{50} \quad \text{(Equation 2)}$$

Figure 3:
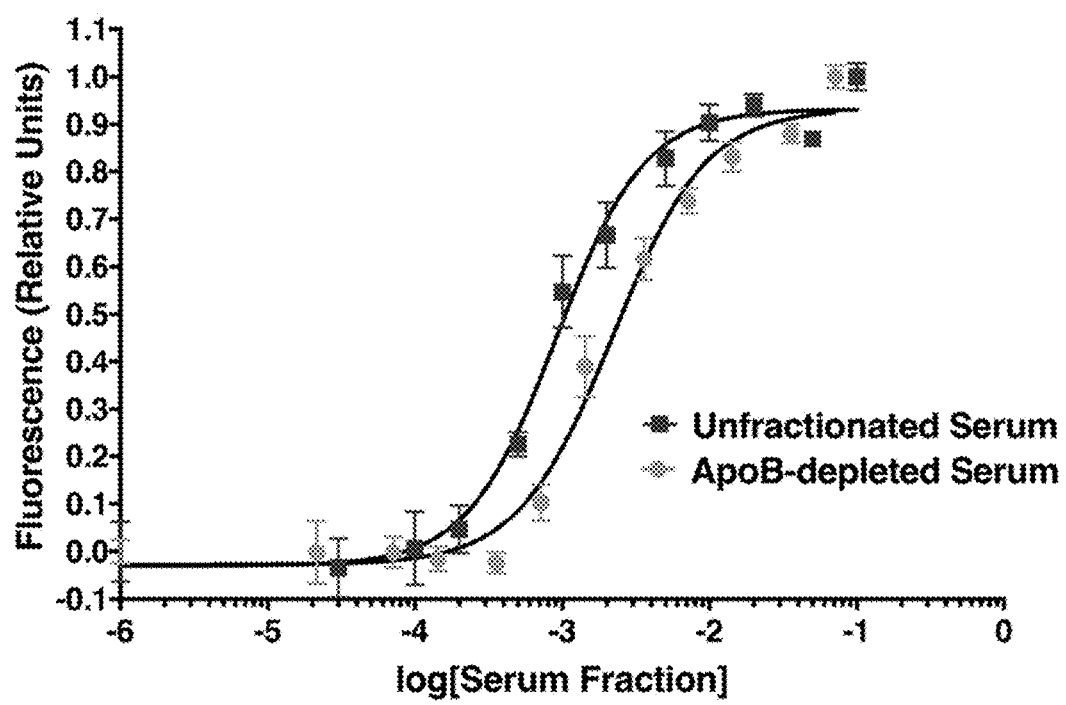
FIG. 3 shows serum or ApoB-depleted serum that was titrated into a solution of 20 nM NP and 125 nM BODIPY-Cholesterol. The effective $K_D$ of serum in this case was calculated as $1.4 \times 10^{-4}$, and of ApoB-depleted serum as $3.0 \times 10^{-4}$. Error bars denote standard deviations of technical quadruplicates.

$EC_{50}$ is the fraction of serum in the reaction needed to recover half-maximal fluorescence. Serum or ApoB-depleted serum were titrated into solutions containing 20 nM lipidated NP and 125 nM BODIPY-Cholesterol, and incubated at 37° C. for 4 hours, by which point equilibrium was reached (FIG. 3). The $EC_{50}$ for whole serum was $1.1 \times 10^{-3}$, and was $2.2 \times 10^{-3}$ for ApoB-depleted serum, yielding an effective $K_D$ for whole serum of $1.4 \times 10^{-4}$ and an effective $K_D$ for ApoB-depleted serum of $3.0 \times 10^{-4}$ (dimensionless units).

Because Equation 2 relies on several simplifying assumptions regarding binding site occupancy and free ligand concentration, further assessment of the validity of $K_{D,serum}$ determinations was performed by solving the exact cubic form of the competition equilibrium algebraically, then using non-linear least-squares regression to determine $K_D$ as described herein. The effective $K_D$ for whole serum by this method was $1.4 \times 10^{-4}$ and for ApoB-depleted serum was $3.1 \times 10^{-4}$. Thus $K_{D,serum}$ as assessed by Equation 2 was in excellent agreement with determinations by fitting to the exact formula.

Using the method reported herein, it is possible to calculate the $K_D$ of cholesterol on a molar basis to a given cholesterol acceptor such as free ApoA1 or a pure fraction of HDL. Using a concentration of ~34 µM HDL in serum,[12] the apparent $K_D$ for cholesterol per mol HDL is approximately 10 nM, which compares favorably to the $K_D$ of NP for cholesterol.

Values for the $K_D$ of cholesterol interactions with lipoproteins have not previously been reported. However, the strength of the interaction reported here compares well to the strength of porphyrin interactions with low density lipoprotein ($K_D$=20 nM), as measured by quenching of porphyrin ring autofluoresence upon interaction with low density lipoprotein.[13] Thus this technique allows for calculation of previously unreported $K_D$ values, and may be extended to further refine understanding of cholesterol binding equilibria with lipoprotein species. However for clinical applications, simple measurement of the $K_D$ in rapidly attainable bulk matrices such as serum or ApoB-depleted serum may be sufficient or even desirable. Reporting $K_D$ as an affinity constant ($K_A$) yields, in this example, a $K_A$ for whole serum of 7100 and for ApoB-depleted serum of 3300, meaningful and readily comprehensible integers with higher values meaning tighter binding, features that make $K_A$ particularly well-suited for direct interpretation and implementation in clinical practice. Finally, this method can be extended to ascertain binding properties of complex matrices for other lipophilic fluorescently-labeled ligands such as testosterone or cortisol.

In summary, the synthesis of a lipid nanostructure has been reported which allows for the measurement of $K_D$ of cholesterol with serum and serum fractions. To our knowledge, $K_D$ of serum for cholesterol has not been previously reported. Measurement of this parameter in various fractions of serum will facilitate construction of more accurate models of cholesterol flux. Furthermore this method is rapid, straightforward, and automatable and therefore will find clinical utility in improving prediction of patients at risk for pathologies dependent upon cholesterol overload, such as certain forms of heart disease.

Example 2

Calculations and Nonlinear Regression Analysis $$[Chol]_f = \frac{-(n_{NP,Chol} + K_{D,NP} - [Chol]_T) + \sqrt{(n_{NP,Chol}[NP] + K_{D,NP} - [Chol]_T) + 4K_D - [Chol]_T}}{2} \quad \text{(Equation 1)}$$

Equation 1 was derived from algebraic manipulation of the following fundamental equations:

$$[Chol]_f = [Chol]_T + [Chol]_{Bound,NP} \quad \text{(Equation S1)}$$

$$K_{D,NP} = \frac{[Chol]_f(n_{NP,Chol}[NP] - [Chol]_{Bound,NP})}{[Chol]_{Bound,NP}} \quad \text{(Equation S2)}$$

Where $[Chol]_{Bound,NP}$ is the concentration of cholesterol bound to the nanoparticle. Note that the term ($n_{NP,chol}[NP]-[Chol]_{Bound,NP}$) denotes the concentration of free cholesterol binding sites in the reaction.

Nonlinear regression analysis for Equation 1 was performed using GraphPad Prism 6 (La Jolla, Calif.) for the parameters $n_{NP,Chol}$ and $K_{D,NP}$ by inputing a custom equation in the non-linear regression fit package:

$$Y=((Ltotal-Kd-n*10^\wedge X+(4*Ltotal*Kd+(-Ltotal+Kd+n*10^\wedge X)^\wedge 2)^\wedge 0.5)/2) \quad \text{(Equation S3)}$$

Where Y is free cholesterol, X is log[NP], n is $n_{NP,Chol}$, Ltotal is $[Chol]_T$.

To test whether Equation 2 is valid under experimental conditions used, where binding site occupancy may be a concern, the exact cubic root of the following system of equations was found using Mathematica 9.0 (Champaign, Ill.). These equations are given below in a format suitable for direct programming into Mathematica.

kdnpeq:=kdnp==(cf)(nnp*npt−cbnp)/cbnp;

kdseq:=kds==(cf)(ns*st−cbs)/cbs;

cteq:=ct==cf+cbs+cbnp;

This system of equations defines the following terms:
kdnp—Kd of the Nanoparticle
cf—free cholesterol concentration
nnp—number of binding sites on the nanoparticle
npt—total amount of nanoparticle in the reaction
cbnp—amount of cholesterol bound to the nanoparticle==> (nnp*npt−cbnp) thus equals free binding sites on the nanoparticle and accounts for binding site depletion.
Similarly:
kds—Kd of Serum
ns—number of binding sites on serum. This is for completeness we model \ this lumped sum parameter as 1 binding site
st—total amount of serum
cbs—cholesterol bound to serum==>(ns*st−cbs) thus equals free binding sites in serum and accounts for binding site depletion.

Finally:
ct=Total cholesterol
cf=free cholesterol
cbs=cholesterol bound to serum
cbnp=cholesterol bound to nanoparticle.

The system has 3 equations, and thus two variables can be eliminated. cf and cbs were selected for elimination, as cbnp is the direct read of quenching and the assay measurement. From prior assay determinations we kdnp and nnp are known. ct and npt can be controlled. st is manipulated as the titrate. ns in this instance is set to 1. Thus, an equation can be solved for which only needs kds to be fit as a parameter.

Eliminate[{kdnpeq, kdseq, cteq}, {cf, cbs}]

Algebraically eliminates cf and cbs from the system of equations, yielding the cubic function:

ct (−cbnp kdnp+cbnp kds+kdnp nnp npt−2 kds nnp npt+(kds nnp^2 npt^2)/cbnp))==−cbnp^2 kdnp+cbnp kdnp^2+cbnp^2 kds−cbnp kdnp kds+cbnp kdnp nnp npt−2 cbnp kds nnp npt+kdnp kds nnp npt+kds nnp^2 npt^2−cbnp kdnp ns st+kdnp nnp npt ns st This is set to be an equation, cbnpeq, which is then solved for cbnp, which is essentially a direct readout of the assay.
Solve[cbnpeq, cbnp]
Yields one real root:

{cbnp -> − ((−ct kdnp − kdnp^2 + ct kds + kdnp kds − kdnp nnp npt + 2 kds nnp npt + kdnp ns st)/(
3 (kdnp − kds))) − (2^(
1/3) (− (− ct kdnp − kdnp^2 + ct kds + kdnp kds − kdnp nnp npt + 2 kds nnp npt + kdnp ns st)^2 +
3 (kdnp − kds) (ct kdnp nnp npt − 2 ct kds nnp npt − kdnp kds nnp npt − kds nnp^2 npt^2 − kdnp nnp npt ns st)))/(3 (kdnp − kds) (2 ct^3 kdnp^3 +
6 ct^2 kdnp^4 + 6 ct kdnp^5 + 2 kdnp^6 − 6 ct^3 kdnp^2 kds −
18 ct^2 kdnp^3 kds − 18 ct kdnp^4 kds − 6 kdnp^5 kds +
6 ct^3 kdnp kds^2 + 18 ct^2 kdnp^2 kds^2 + 18 ct kdnp^3 kds^2 +
6 kdnp^4 kds^2 − 2 ct^3 kds^3 − 6 ct^2 kdnp kds^3 −
6 ct kdnp^2 kds^3 − 2 kdnp^3 kds^3 − 3 ct^2 kdnp^3 nnp npt +
3 ct kdnp^4 nnp npt + 6 kdnp^5 nnp npt + 12 ct^2 kdnp^2 kds nnp npt −
3 ct kdnp^3 kds nnp npt − 15 kdnp^4 kds nnp npt −
15 ct^2 kdnp kds^2 nnp npt − 3 ct kdnp^2 kds^2 nnp npt +
12 kdnp^3 kds^2 nnp npt + 6 ct^2 kds^3 nnp npt +
3 ct kdnp kds^3 nnp npt − 3 kdnp^2 kds^3 nnp npt −
3 ct kdnp^3 nnp^2 npt^2 + 6 kdnp^4 nnp^2 npt^2 −
3 ct kdnp^2 kds nnp^2 npt^2 − 12 kdnp^3 kds nnp^2 npt^2 +
12 ct kdnp^2 kds^2 nnp^2 npt^2 + 3 kdnp^2 kds^2 nnp^2 npt^2 −
6 ct kds^3 nnp^2 npt^2 + 3 kdnp^2 kds^2 nnp^2 npt^2 +
2 kdnp^3 nnp^3 npt^3 − 3 kdnp^2 kds nnp^3 npt^3 −
3 kdnp kds^2 nnp^3 npt^3 + 2 kds^3 nnp^3 npt^3 −
6 ct^2 kdnp^3 ns st − 12 ct kdnp^4 ns st − 6 kdnp^5 ns st +
12 ct^2 kdnp^2 kds ns st + 24 ct kdnp^3 kds ns st +
12 kdnp^4 kds ns st − 6 ct^2 kdnp kds^2 ns st −
12 ct kdnp^2 kds^2 ns st − 6 kdnp^3 kds^2 ns st +
6 ct kdnp^3 nnp npt ns st − 3 kdnp^4 nnp npt ns st −
9 ct kdnp^2 kds nnp npt ns st + 9 kdnp^3 kds nnp npt ns st +
3 ct kdnp kds^2 nnp npt ns st − 6 kdnp^2 kds^2 nnp npt ns st +
3 kdnp^3 nnp^2 npt^2 ns st − 12 kdnp^2 kds nnp^2 npt^2 ns st +
3 kdnp kds^2 nnp^2 npt^2 ns st + 6 ct kdnp^3 ns^2 st^2 +
6 kdnp^4 ns^2 st^2 − 6 ct kdnp^2 kds ns^2 st^2 −
6 kdnp^3 kds ns^2 st^2 − 3 kdnp^3 nnp npt ns^2 st^2 −
3 kdnp^2 kds nnp npt ns^2 st^2 − 2 kdnp^3 ns^3 st^3 +
□((2 ct^3 kdnp^3 + 6 ct^2 kdnp^4 + 6 ct kdnp^5 + 2 kdnp^6 −
6 ct^3 kdnp^2 kds − 18 ct^2 kdnp^3 kds − 18 ct kdnp^4 kds −
6 kdnp^5 kds + 6 ct^3 kdnp kds^2 + 18 ct^2 kdnp^2 kds^2 +
18 ct kdnp^3 kds^2 + 6 kdnp^4 kds^2 − 2 ct^3 kds^3 −
6 ct^2 kdnp kds^3 − 6 ct kdnp^2 kds^3 − 2 kdnp^3 kds^3 −
3 ct^2 kdnp^3 nnp npt + 3 ct kdnp^4 nnp npt + 6 kdnp^5 nnp npt +
12 ct^2 kdnp^2 kds nnp npt − 3 ct kdnp^3 kds nnp npt −
15 kdnp^4 kds nnp npt − 15 ct^2 kdnp kds^2 nnp npt −
3 ct kdnp^2 kds^2 nnp npt + 12 kdnp^3 kds^2 nnp npt +
6 ct^2 kds^3 nnp npt + 3 ct kdnp kds^3 nnp npt −
3 kdnp^2 kds^3 nnp npt − 3 ct kdnp^3 nnp^2 npt^2 +
6 kdnp^4 nnp^2 npt^2 − 3 ct kdnp^2 kds nnp^2 npt^2 −
12 kdnp^3 kds nnp^2 npt^2 + 12 ct kdnp^2 kds^2 nnp^2 npt^2 +
3 kdnp^2 kds^2 nnp^2 npt^2 − 6 ct kds^3 nnp^2 npt^2 +
3 kdnp kds^3 nnp^2 npt^2 + 2 kdnp^3 nnp^3 npt^3 −
3 kdnp^2 kds nnp^3 npt^3 − 3 kdnp kds^2 nnp^3 npt^3 +
2 kds^3 nnp^3 npt^3 − 6 ct^2 kdnp^3 ns st − 12 ct kdnp^4 ns st −
6 kdnp^5 ns st + 12 ct^2 kdnp^2 kds ns st +
24 ct kdnp^3 kds ns st + 12 kdnp^4 kds ns st −
6 ct^2 kdnp kds^2 ns st − 12 ct kdnp^2 kds^2 ns st −
6 kdnp^3 kds^2 ns st + 6 ct kdnp^3 nnp npt ns st −
3 kdnp^4 nnp npt ns st − 9 ct kdnp^2 kds nnp npt ns st +
9 kdnp^3 kds nnp npt ns st + 3 ct kdnp kds^2 nnp npt ns st −
6 kdnp^2 kds^2 nnp npt ns st + 3 kdnp^3 nnp^2 npt^2 ns st +
12 kdnp^2 kds nnp^2 npt^2 ns st + 3 kdnp kds^2 nnp^2 npt^2 ns st +
6 ct kdnp^3 ns^2 st^2 + 6 kdnp^4 ns^2 st^2 −

4 (− (−ct kdnp − kdnp^2 + ct kds + kdnp kds − kdnp nnp npt +
2 kds nnp npt + kdnp ns st)^2 +
3 (kdnp − kds) (ct kdnp nnp npt − 2 ct kds nnp npt −
kdnp kds nnp npt − kds nnp^2 npt^2 −
kdnp nnp npt ns st))^3))^(1/3)) +
1/(3 2^(
1/3) (kdnp − kds)) (2 ct^3 kdnp^3 + 6 ct^2 kdnp^4 + 6 ct kdnp^5 +
2 kdnp^6 − 6 ct^3 kdnp^2 kds − 18 ct^2 kdnp^3 kds − 18 ct kdnp^4 kds −
6 kdnp^5 kds + 6 ct^3 kdnp kds^2 + 18 ct^2 kdnp^2 kds^2 +
18 ct kdnp^3 kds^2 + 6 kdnp^4 kds^2 − 2 ct^3 kds^3 −
6 ct^2 kdnp kds^3 − 6 ct kdnp^2 kds^3 − 2 kdnp^3 kds^3 −
3 ct^2 kdnp^3 nnp npt + 3 ct kdnp^4 nnp npt + 6 kdnp^5 nnp npt +
12 ct^2 kdnp^2 kds nnp npt − 3 ct kdnp^3 kds nnp npt −
15 kdnp^4 kds nnp npt − 15 ct^2 kdnp kds^2 nnp npt −
3 ct kdnp^2 kds^2 nnp npt + 12 kdnp^3 kds^2 nnp npt +
6 ct^2 kds^3 nnp npt + 3 ct kdnp kds^3 nnp npt −
3 kdnp^2 kds^3 nnp npt − 3 ct kdnp^3 nnp^2 npt^2 +
6 kdnp^4 nnp^2 npt^2 − 3 ct kdnp^2 kds nnp^2 npt^2 −
12 kdnp^3 kds nnp^2 npt^2 + 12 ct kdnp^2 kds^2 nnp^2 npt^2 +
3 kdnp^2 kds^2 nnp^2 npt^2 − 6 ct kds^3 nnp^2 npt^2 +
3 kdnp kds^3 nnp^2 npt^2 + 2 kdnp^3 nnp^3 npt^3 −
3 kdnp^2 kds nnp^3 npt^3 − 3 kdnp kds^2 nnp^3 npt^3 +
2 kds^3 nnp^3 npt^3 − 6 ct^2 kdnp^3 ns st − 12 ct kdnp^4 ns st −
6 kdnp^5 ns st + 12 ct^2 kdnp^2 kds ns st +
24 ct kdnp^3 kds ns st + 12 kdnp^4 kds ns st −
6 ct^2 kdnp kds^2 ns st − 12 ct kdnp^2 kds^2 ns st −
6 kdnp^3 kds^2 ns st + 6 ct kdnp^3 nnp npt ns st −
3 kdnp^4 nnp npt ns st − 9 ct kdnp^2 kds nnp npt ns st +
9 kdnp^3 kds nnp npt ns st + 3 ct kdnp kds^2 nnp npt ns st −
6 kdnp^2 kds^2 nnp npt ns st + 3 kdnp^3 nnp^2 npt^2 ns st +
12 kdnp^2 kds nnp^2 npt^2 ns st + 3 kdnp kds^2 nnp^2 npt^2 ns st +
6 ct kdnp^3 ns^2 st^2 + 6 kdnp^4 ns^2 st^2 −

-continued

```
6 ct kdnp^2 kds ns^2 st^2 − 6 kdnp^3 kds ns^2 st^2 −
    3 kdnp^3 nnp npt ns^2 st^2 − 3 kdnp^2 kds nnp npt ns^2 st^2 −
    2 kdnp^3 ns^3 st^3)^2 +
4 (− (−ct kdnp − kdnp^2 + ct kds + kdnp kds − kdnp nnp npt +
    2 kds nnp npt + kdnp ns st)^2 +
3 (kdnp − kds) (ct kdnp nnp npt − 2 ct kds nnp npt −
    kdnp kds nnp npt − kds nnp^2 npt^2 − kdnp nnp npt ns st))^3))^(
1/3)}
```

Figure 5:
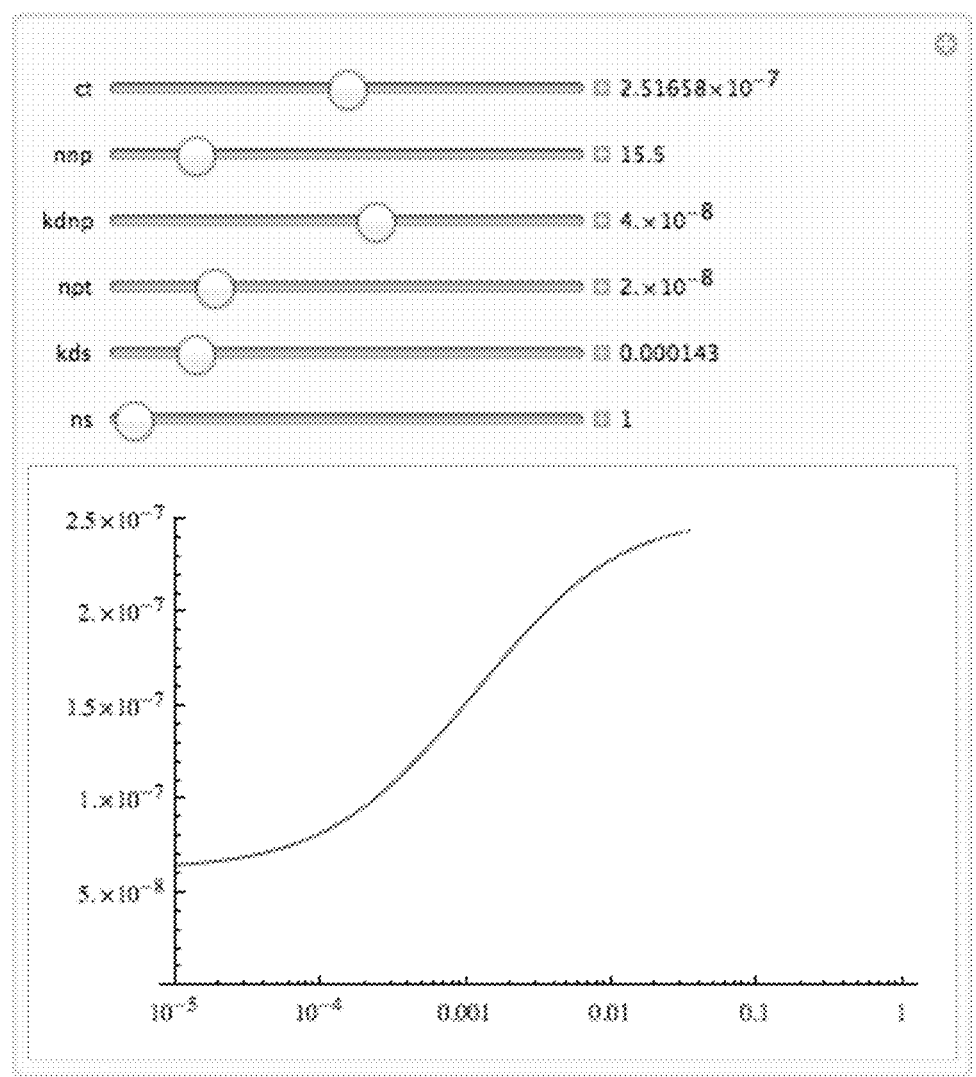
FIG. 5 shows the manipulate function in Mathematica that was used to assess the performance and plausibility of the function generated from solving a system of binding equations. This allowed for assessment of function performance as well as manual estimation of initial starting parameters for KD.
Figure 6:
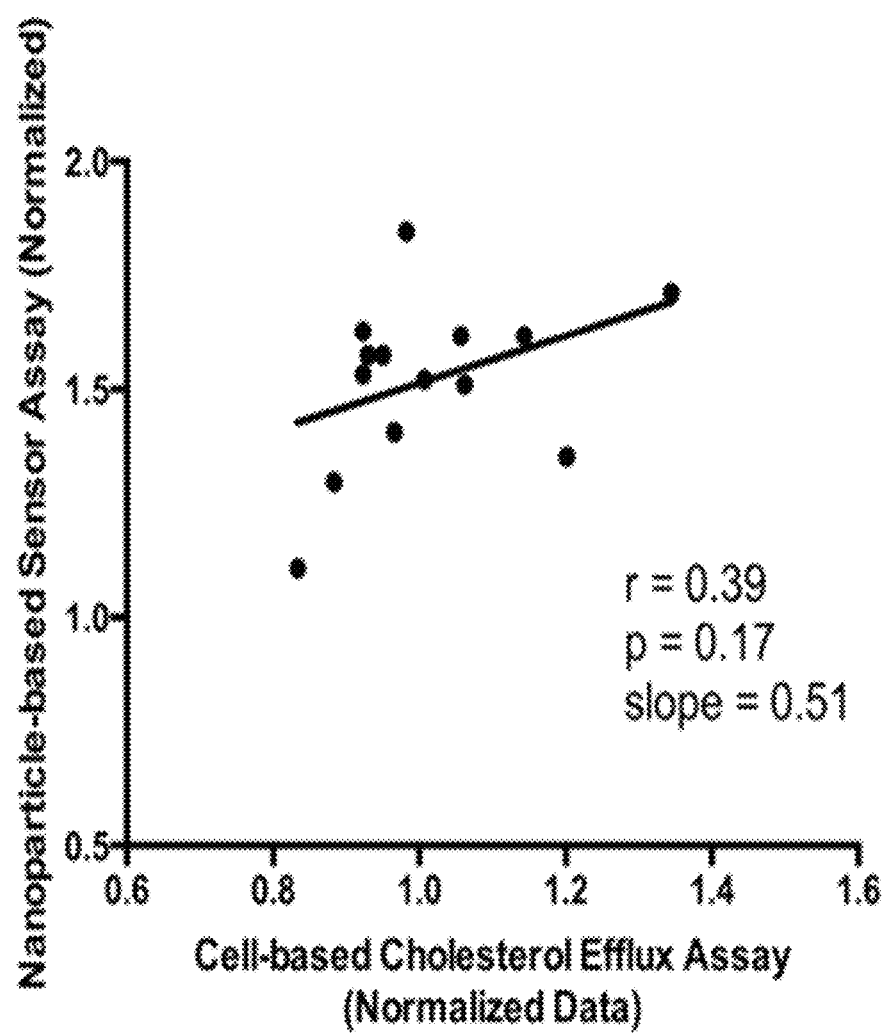
FIG. 6 shows an assay measuring patient serum affinity for cholesterol binding. The data show a correlation between the performance of the assay of the invention and a currently accepted assay. The normalized efflux assay is plotted on the x-axis, and can be seen to vary in magnitude among participants from approximately 0.8 to approximately 1.4, approximately 1.0 to approximately 2.0, or approximately 0.8 to approximately 2.4 with a value of 1.0 being equivalent to the efflux value of the pooled sample.

To assess the performance of the function and how it performs with real parameters, the manipulate function is used (FIG. 5). For example:

```
Manipulate[LogLinearPlot[ct−(Cubic Root Argument
    noted above), {st, 1*^−5, 1*^0}, PlotRange
    →{0, 250*10^−9}], {ct, 1*^−9, 500*^−9,
    Appearance→"Labeled"}, {nnp, 1, 100,
    Appearance→"Labeled"}, {kdnp, 0.1*^−9, 7*^−
    8, Appearance→"Labeled"}, {npt, 1*^−9,
    100*^−9, Appearance→"Labeled"}, {kds,
    0.0000001, 0.001, Appearance→"Labeled"},
    {ns, 1, 10, Appearance→"Labeled"}]
```

This allows assessment of function performance as well as allows manual estimation of initial starting parameters for $K_D$.

Next non-linear regression is performed. Although the root of the function is real, it contains imaginary parts which makes the built-in NonlinearModelFit function return an error because rounding errors lead to the return of a complex number with an extremely small imaginary part, which disallows correct execution of the function.

Therefore, optimization was done semi-manually as follows using the following standard method for least-squares error functions:

$$\text{Error} = \sum_{i}^{n} (observed_i - predicted_i)^2 \quad \text{(Equation S4)}$$

To find the minimum value of this function, $K_D$ was stepped over a range of values until the minimum was found to a precision of 4 digits for $K_D$. Initial choice of the range of $K_D$ to test is guided by $K_D$ values generated by standard $EC_{50}$ analysis, for example as implemented in GraphPad Prism.

An example of the stepping argument which generates a list of Errors for incrementally different values of $K_D$:

```
Do[Print[j]
    Print[Sum[(data[[i, 2]] −
        f3[250.*^−9, 15., 40.*^−9, 20.*^−9, j, 1, data[[i, 1]]])^2, {i,
        1, 48}]],
{j, 0.0001, 0.0005, 0.000005}]
```

Where data is an array containing the experimental data with serum concentration in column 1 and free cholesterol readings in column 2. The argument {i, 1, 48} steps the function f3 (which contains the binding equation solution) through the 48 data points in this data set. The argument {j, 0.0001, 0.0005, 0.000005} steps the value of $K_D$ from 0.0001 to 0.0005 in 0.000005 increments. A list of errors is printed and the minimum error is found. Using this exact method, $K_D$ for serum and ApoB-depleted serum were found as reported herein. The values found by Equation 2 compared very favorably to these.

Example 3

Assay Measuring Patient Serum Affinity for Cholesterol Binding

An experiment was performed to compare the methods of the invention with currently used methods. The data suggest a correlation between the two assays. The assay of the invention performed consistently and in a similar manner to the currently accepted assay.

In this experiment, 14 healthy donors donated 10 ml serum for further study. This serum was collected in the conventional manner using needles and a vacutainer tube. Using this serum, a conventional cholesterol efflux assay using J774 macrophages and radiolabled cholesterol ($^3$H-labelled cholesterol) was performed. (A. V. Khera, M. Cuchel, M. de la Llera-Moya, A. Rodrigues, M. F. Burke, K. Jafri, B. C. French, J. A. Phillips, M. L. Mucksavage, R. L. Wilensky, E. R. Mohler, G. H. Rothblat and D. J. Rader, *The New England journal of medicine*, 2011, 364, 127-135.)

The radiolabelled cholesterol assay was performed as follows:

Sample preparation for cholesterol efflux assay. Frozen serum aliquots from participants were gently thawed by room temperature incubation. 60 µl of serum was pipetted into a microcentrifuge tube. To precipitate ApoB-containing lipoproteins from the sample, 24 µl of PEG solution (20% w/v of Polyethylene Glycol 8000 (Sigma-Aldrich, Saint Louis, Mo.), 200 mM glycine, pH 7.4) was added and mixed by gently flicking the tube. After a 20 minute room temperature incubation, the mixture was centrifuged at 12,700×g for 30 minutes at 4° C. To create the final efflux media, 50.4 µl of the supernatant was then added to 1750 µl MEM media with 25 mM HEPES buffer, 30 µM of cAMP analog (8-(4-Cholorphenylthio)adenosine 3',5'-cyclic monophosphate sodium salt, Sigma-Aldrich, Saint Louis, Mo.), and 2 µg/ml Acyl-CoA Cholesterol Acyl Transferase (ACAT) inhibitor (Sandoz 58-035, Sigma-Aldrich, Saint Louis, Mo.). This results in an efflux medium with 2.0% final concentration of Apo-B depleted serum, in sufficient volume for technical triplicates at 500 µl each.

Efflux Assay. Cholesterol efflux from cells to patient serum was measured using the assay developed by Rothblat, et al. J774 mouse macrophages were plated on 24-well plates at 150,000 cells per well on day 1. On day 2, the cells were radiolabeled with $^3$H-Cholesterol at 2 µCi/ml by incubating each well in 500 ul of RPMI media with 5% FBS and $^3$H-Cholesterol (Perkin-Elmer, Waltham, Mass.). After overnight incubation, to upregulate cholesterol efflux, cells were treated with 2 ug/ml ACAT inhibitor, 300 µM cAMP analog in RPMI medium with 5% bovine serum albumin for 18 hours. On day 4, the efflux assay was performed. Efflux medium prepared from participant serum was placed on cells in technical triplicate at a volume of 500 µl per well. After four hours, 300 ul of the medium was aspirated and filtered to remove cellular debris. 250 ul of the filtered medium was assayed for radioactivity by scintillation counting. Total radioactivity was assessed by counting radioactivity in cells after isopropanol extraction. Percent efflux for each sample was calculated as follows: (radioactivity in the medium after efflux—radioactivity in blank medium lacking serum)/(total radioactivity in labeled cells). The percent efflux for the technical triplicates was averaged together. To normalize these efflux results across sample runs, a serum sample pool drawn from healthy volunteers was run with each sample. Normalized efflux was calculated as percent efflux for the sample divided by percent efflux for the sample pool. This normalized efflux value for each participant was then used for further association and correlation analysis.

In this example, the normalized efflux assay was plotted on the x-axis, and could be seen to vary in magnitude among participants from approximately 0.8 to approximately 1.4, with a value of 1.0 being equivalent to the efflux value of the pooled sample.

Nanoparticle Assay: In parallel experiments, the nanoparticle-based sensor assay discussed here was performed. In this particular experiment, nanoparticles at a concentration of 30 uM, BODIPY-cholesterol at a concentration of 250 nM, and Apo- B depleted serum (prepared as described above) at a final concentration of 2% were mixed together in a total volume of 200 ul and allowed to incubate overnight in a 96-well plate. Mixtures were prepared in duplicate for each of the 14 participants. Background control wells lacking any serum (to measure maximum quenched signal in the presence of nanoparticle) were also prepared. After overnight incubation, fluorescence was read using a 96-well plate reading fluorimeter, at an excitation wavelength of 485 nm and an emission wavelength of 520 nm.

For each sample, from these fluorescence values was subtracted the background control fluorescence value to arrive at signal for each serum, with higher signal reflecting enhanced ability of the participant's serum to compete with the nanoparticle for BODIPY-cholesterol. This value was normalized to the background-subtracted fluorescence value of the plasma pool, and plotted on the y-axis. It can be seen that the normalized nanoparticle-based sensor assay value ranges from approximately 1.0 to 2.0. It can further be seen from the graph that there is a correlation between the two assays, with an r value of 0.39, and a slope of 0.51, and a p=0.17, which is close to statistical significance.

The analysis method in this example is different than the one described above. It can be readily appreciated that serum with a greater ability to compete with nanoparticle for binding cholesterol will at any given serum concentration be equal to that of serum with a lesser ability to compete with nanoparticle for binding cholesterol, lead to greater dequenching of serum BODIPY-cholesterol binding, and lead to a higher fluorescence value after correcting for background.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

REFERENCES (1) Lusis, A. J. Nature 2000, 407, 233.
(2) Rosenson, R. S.; Brewer, H. B., Jr.; Davidson, W. S.; Fayad, Z. A.; Fuster, V.; Goldstein, J.; Hellerstein, M.; Jiang, X. C.; Phillips, M. C.; Rader, D. J.; Remaley, A. T.; Rothblat, G. H.; Tall, A. R.; Yvan-Charvet, L. Circulation 2012, 125, 1905.
(3) Khera, A. V.; Cuchel, M.; de la Llera-Moya, M.; Rodrigues, A.; Burke, M. F.; Jafri, K.; French, B. C.; Phillips, J. A.; Mucksavage, M. L.; Wilensky, R. L.; Mohler, E. R.; Rothblat, G. H.; Rader, D. J. N Engl J Med 2011, 364, 127.
(4) de la Llera-Moya, M.; Drazul-Schrader, D.; Asztalos, B. F.; Cuchel, M.; Rader, D. J.; Rothblat, G. H. Arteriosclerosis, thrombosis, and vascular biology 2010, 30, 796.
(5) Karlin, J. B.; Johnson, W. J.; Benedict, C. R.; Chacko, G. K.; Phillips, M. C.; Rothblat, G. H. J Biol Chem 1987, 262, 12557.
(6) Thaxton, C. S.; Daniel, W. L.; Giljohann, D. A.; Thomas, A. D.; Mirkin, C. A. J Am Chem Soc 2009, 131, 1384.
(7) Luthi, A. J.; Zhang, H.; Kim, D.; Giljohann, D. A.; Mirkin, C. A.; Thaxton, C. S. ACS Nano 2012, 6, 276.
(8) Dubertret, B.; Calame, M.; Libchaber, A. J. Nat. Biotechnol. 2001, 19, 365.
(9) Seferos, D. S.; Giljohann, D. A.; Hill, H. D.; Prigodich, A. E.; Mirkin, C. A. Journal of the American Chemical Society 2007, 129, 15477.
(10) Demers, L. M.; Mirkin, C. A.; Mucic, R. C.; Reynolds, R. A.; Letsinger, R. L.; Elghanian, R.; Viswanadham, G. Anal. Chem. 2000, 72, 5535.
(11) Pollard, T. D. Mol Biol Cell 2010, 21, 4061.
(12) Mackey, R. H.; Greenland, P.; Goff, D. C., Jr.; Lloyd-Jones, D.; Sibley, C. T.; Mora, S. Journal of the American College of Cardiology 2012, 60, 508.
(13) Bonneau, S.; Vever-Bizet, C.; Morliere, P.; Maziere, J. C.; Brault, D. Biophys J 2002, 83, 3470.

What is claimed is:

1. A method for measuring the equilibrium constant of an acceptor for a lipophilic or amphiphilic molecule, comprising:

(a) providing the lipophilic or amphiphilic molecule having detectable signal;
(b) providing a structure, the structure comprising a nanostructure core and a lipid layer surrounding and attached to the nanostructure core, wherein the structure quenches the signal of the molecule when the structure and the molecule are proximate;
(c) providing an acceptor;
(d) allowing the acceptor to compete with the structure for binding with the molecule; and
(e) measuring the signal, wherein the level of the signal correlates with the equilibrium constant of the acceptor for the molecule,
wherein the method is a cell-free method.

2. The method of claim 1, the method further comprising increasing the amount of acceptor provided.

3. The method of claim 1, the method further comprising increasing the amount of structure provided.

4. The method of claim 2, wherein increasing the amount of acceptor provided leads to an increase in signal.

5. The method of claim 3, wherein increasing the amount of structure provided leads to a decrease in signal.

6. The method of claim 1, wherein increasing or decreasing the amount of molecule improves the signal to noise ratio of the system.

7. The method of claim 1, wherein the method is a component of an assay.

8. The method of claim 1, wherein the method is a component of a diagnostic assay.

9. The method of claim 1, wherein the method is a method for assessing cardiovascular risk in a subject.

10. The method of claim 1, wherein the lipid layer is a bilayer.

11. The method of claim 1, wherein the molecule is a steroid or a derivative or analog thereof.

12. The method of claim 1, wherein the molecule is a lipopolysaccharide or a derivative or analog thereof.

13. The method of claim 1, wherein the molecule is a Cholestane, Cholane, Pregnane, Androstane or Estrane or a derivative or analog thereof.

14. The method of claim 1, wherein the molecule is BODIPY-cholesterol.

15. The method of claim 1, wherein the signal is fluorescence.

16. The method of claim 1, wherein the signal is fluorescence polarization.

17. The method of claim 1, wherein the nanostructure core is an inorganic material.

18. The method of claim 1, wherein the nanostructure core is a metal.

19. The method of claim 1, wherein the nanostructure core is gold.

20. The method of claim 1, wherein the structure further comprises apolipoprotein bound to at least the outer surface of the lipid layer.

21. The method of claim 20, wherein the apolipoprotein is apolipoprotein A-I, apolipoprotein A-II, or apolipoprotein E.

22. The method of claim 1, wherein the acceptor is a lipoprotein.

23. The method of claim 1, wherein the acceptor is a high-density lipoprotein (HDL).

24. The method of claim 1, wherein the acceptor is a component of serum.

25. The method of claim 24, wherein the serum is human serum.

26. The method of claim 24, wherein the serum is enriched for HDL.

27. The method of claim 24, wherein the serum is depleted for ApoB.

* * * * *